US011994480B2

(12) United States Patent
Mitchell et al.

(10) Patent No.: US 11,994,480 B2
(45) Date of Patent: May 28, 2024

(54) DIGITAL RETORT MEASUREMENT SYSTEMS AND METHODS

(71) Applicant: Schlumberger Technology Corporation, Sugar Land, TX (US)

(72) Inventors: Jonathan Mitchell, Cambridge (GB); Colin Stewart, Houston, TX (US); Adam Colbourne, Cambridge (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 180 days.

(21) Appl. No.: 17/755,094

(22) PCT Filed: Oct. 22, 2020

(86) PCT No.: PCT/US2020/056747
§ 371 (c)(1),
(2) Date: Apr. 21, 2022

(87) PCT Pub. No.: WO2021/081144
PCT Pub. Date: Apr. 29, 2021

(65) Prior Publication Data
US 2022/0381714 A1    Dec. 1, 2022

Related U.S. Application Data

(60) Provisional application No. 62/924,510, filed on Oct. 22, 2019.

(51) Int. Cl.
*G01N 24/08*  (2006.01)
*G01N 33/28*  (2006.01)
*G01R 33/44*  (2006.01)

(52) U.S. Cl.
CPC ....... *G01N 24/081* (2013.01); *G01N 33/2823* (2013.01); *G01R 33/448* (2013.01)

(58) Field of Classification Search
CPC . G01R 33/448; G01N 24/081; G01N 33/2823
See application file for complete search history.

(56) References Cited

U.S. PATENT DOCUMENTS 6,346,813 B1    2/2002   Kleinberg
6,960,913 B2    11/2005  Heaton
(Continued)

FOREIGN PATENT DOCUMENTS

GB      2542406 A        3/2017
WO      2006088453 A1    8/2006

OTHER PUBLICATIONS

Mitchell, J., "Magnetic resonance diffusion measurements of droplet size in drilling fluid emulsions on a benchtop instrument", Colloids and Surfaces A, 2019, 594, pp. 69-77.
(Continued)

*Primary Examiner* — Gregory H Curran
(74) *Attorney, Agent, or Firm* — Jeffrey D. Frantz

(57) ABSTRACT

Tools and methods are used to determine the oil, water, and solids volume fractions in a drilling fluid at the rig site. The volume fractions can be determined in-line with returned drilling fluid by using an NMR magnet and a flow line or sample chamber that receives a fluid sample and loads it into the NMR magnet. Using an RF probe, spectrometer, and computing device, data processing and interpretation of NMR data from the spectrometer is performed, while also raising a flag when iron contamination exceeds a predefined threshold.

20 Claims, 13 Drawing Sheets

(56) References Cited

U.S. PATENT DOCUMENTS

| | | | | |
|---|---|---|---|---|
| 8,248,067 | B2* | 8/2012 | Ong | G01F 1/716 |
| | | | | 324/303 |
| 9,194,972 | B2 | 11/2015 | Van Der Zwagg | |
| 10,228,336 | B2* | 3/2019 | Seltzer | G01R 33/3808 |
| 10,697,910 | B2 | 6/2020 | Mitchell et al. | |
| 10,983,242 | B2* | 4/2021 | Li | G01N 24/082 |
| 2008/0315873 | A1 | 12/2008 | Ganesan | |
| 2017/0122891 | A1 | 5/2017 | McCarthy et al. | |
| 2017/0343497 | A1 | 11/2017 | Anand et al. | |
| 2018/0003654 | A1 | 1/2018 | Chen et al. | |

OTHER PUBLICATIONS

Mitchell, J. et al, "Emulation of petroleum well-logging D-T2 correlations on a standard benchtop spectrometer", Journal of Magnetic Resonance, 2011, 212, pp. 394-401.

Mitchell, J. et al., "Quantitative Remaining Oil Interpretation Using Magnetic Resonance: From the Laboratory to the Pilot", SPE 154704, presented at the SPE EOR Conference at Oil and Gas West Asia, Muscat, Oman, 2012, 11 pages.

Mitchell, J. et al., "Numerical estimation of relaxation and diffusion distributions in two dimensions", Progress in Nuclear Magnetic Resonance Spectroscopy, 2012, 62, pp. 34-50.

Mitchell, J. et al., "Nuclear magnetic resonance relaxation and diffusion in the presence of internal gradients: The effect of magnetic field strength", Physical Review E, 2010, 81, 026101, 19 pages.

Mitchell, J. et al., "A robust nuclear magnetic resonance workflow for quantitative determination of petrophysical properties from drill cuttings", Journal of Petroleum Science and Engineering, 2019, 174, pp. 351-361.

Mitchell, J. et al., "Low-field permanent magnets for industrial process and quality control", Progress in Nuclear Magnetic Resonance Spectroscopy, 2014, 76, pp. 1-60.

Mitchell, J. et al., "Obtaining true transverse relaxation time distributions in high-field NMR measurements of saturated porous media: Removing the influence of internal gradients", Journal of Chemical Physics, 2010, 132, 10 pages.

Mitchell, J. , "Can sodium provide more than a tracer for brine in petrophysics", Journal of Petroleum Science and Engineering, 2016, 146, pp. 360-368.

Mitchell, J. et al., "Sodium-23 NMR in porous media", Microporous Mesoporous Materials, 2018, 269, pp. 109-112.

Powles, J. G. et al., "Double-Pulse Nuclear-Resonance Transients in Solids", Physics Letters, 1962, 2(2), pp. 58-59.

Rismanto, R. et al., "Explorative Study of NMR Drilling Fluids Measurement", Annual Transactions of the Nordic Rheology Society, 2007, 15, 7 pages.

Romanenko, K. V. et al., "35Cl profiling using centric scan Sprite with variable flip angle excitation", Journal of Magnetic Resonance, 2009, 198, pp. 24-30.

Ropp, C. et al., "Electropermanent magnets for variable-field NMR", Journal of Magnetic Resonance, 2019, 303, pp. 82-90.

Singer, P. M. et al., "Low magnetic fields for flow propagators in permeable rocks", Journal of Magnetic Resonance, 2006, 183, 167-177.

Song, Y-Q. et al., "T1-T2 Correlation Spectra Obtained Using a Fast Two-Dimensional Laplace Inversion", Journal of Magnetic Resonance, 2002, 154(2), pp. 261-268.

Tang, W. et al., "A single-board NMR spectrometer based on a software defined radio architecture", Measurement Science and Technology, 2011, 8 pages.

Trout, S. R., "Material Selection of Permanent Magnets, Considering Thermal Properties Correctly", presented at the Electric Manufacturing and Coil Winding Conference in Cincinnati, Ohio, 2001, 6 pages.

Utsuzawa, S. et al., "Transformer-coupled NMR probe", Journal of Magnetic Resonance, 2012, 216, pp. 128-133.

Valori, A. et al., "Digital filters for low-field NMR", Concepts in Magnetic Resonance, 2016, 46B, pp. 202-220.

Venkataramanan, L. et al., "Solving Fredholm integrals of the First Kind with Tensor Product Structure in 2 and 2.5 Dimensions", IEEE Transactions on Signal Processing, 2002, 50(5), pp. 1017-1026.

Venkataramanan, L. et al., "An Unsupervised Learning Algorithm to Compute Fluid Volumes from NMR T1-T2 Logs in Unconventional Reservoirs", Petrophysics, 2018, 59(5), pp. 61-632.

Vold, R. L. et al., "Measurement of Spin Relaxation in Complex Systems", Journal of Chemical Physics, 19368, 48, pp. 3831-3832.

Wilson, J. D., "Statistical approach to the solution of first kind integral-equations arising in the study of materials and their properties", Journal of Materials Science, 1992, 27, pp. 3911-3924.

Yarman, C. E. et al., "A greedy variational approach for generating sparse T1-T2 NMR relaxation time distributions", Journal of Magnetic Resonance, 2019, 301, pp. 94-100.

Zhang, R. et al., "Emulsification properties of comb-shaped trimeric nonionic surfactant for high temperature drilling fluids based on water in oil", Colloids and Surfaces A: Physiochemical Engineering Aspects, 2017, 520, pp. 855-863.

API Recommended Practice 13B-2 "Recommended Practice for Field Testing Oil-based Drilling Fluids", 2014, Chapter 9: Retort Test for Oil, Water, and Solids Concentrations, 19 pages with Title Page and Index.

Fukushima, E. et al., "How to Set Pulse Lengths", Chapter VI. A. 3, in Experimental Pulse NMR: A Nuts and Bolts Approach, Addison-Wesley Publishing Company Inc., Reading MA, USA, 1981, pp. 434-437.

Press, W. H. et al., "Nonlinear Models", Chapter 15.5 in Numerical Recipes in Fortran 77, Cambridge University Press, Cambridge, UK, 1986, pp. 675-683.

"Raspberry Pi 4", product description downloaded from Raspberry Pi on May 9, 2022 at https://www.raspberrypi.org/products/, 11 pages.

"SK-FT843-W—Starter Kit", product discription downloaded from 4D Systems on May 9, 2022 at https://4dsystems.com.au/, 3 pages.

"MS2/MS3 System", product discription downloaded from Barrington Instruments on May 9, 2022 at https://www.bartington.com/ms2-ms3/, 3 pages.

"Halbach array", from Wilkipedia on May 9, 2022 at https://en.wikipedia.org/wiki/Halbach_array#Halbach_cylinder, 7 pages.

"Rock Core Imaging", product discription downloaded from MR Solutions on May 9, 2022 at http://www.mrsolutions.com/products/imaging-systems/imacore/, 2 pages.

"Spinsolve 43 with active 13C/129Xe switch on the X-channel at EPFL, Lifmet", from Magritek on May 9, 2022 at http://www.magritek.com/products/spinsolve/, 3 pages.

Fukushima, E. et al., "Spectrometers and Components, Chapter V. in Experimental Pulse NMR: A Nuts and Bolts Approach", Addison-Wesley Publishing Company Inc., Reading MA, USA, 1981, pp. 358-367.

Sorland, G. H., "The Discrete Approach for 1- and 2-Dimensional Data analysis, the anahess", Chapter 5.3 in Dynamic Pulsed-Field-Gradient NMR, Springer-Verlag, Berlin, 2014, p. 139.

Collinson, D. W., "High- and low-temperature measurements" Chapter 4 in Methods in rock magnetism and palaeomagnetism: Techniques and instrumentation, 1983, Chapman & Hall, New York, pp. 104-117.

Collinson, D. W., "Initial magnetic susceptibility" Chapter 2 in Methods in rock magnetism and palaeomagnetism: Techniques and instrumentation, 1983, Chapman & Hall, New York, pp. 14-58.

International Search Report and Written Opinion in International Patent Application No. PCT/US2020/056747, dated Feb. 18, 2021, 11 pages.

International Preliminary Report on Patentability in International Patent Application No. PCT/US2020/056747, dated May 5, 2022, 8 pages.

Direct Industry, "PTC heating element HP series", accessible at https://www.directindustry.com/prod/dbk-industrial-thermal-management/product-55943-2379297.html, 2 pages.

(56) References Cited

OTHER PUBLICATIONS

Blumler, P., "Proposal for a Permanent Magnet System with a Constant Gradient Mechanically Adjustable in Direction and Strength", Concepts in Magnetic Resonance Engineering, 2016, 46(1), pp. 41-48.
Borgia, G. C. et al., "Uniform-Penalty Inversion of Multiexponential Decay Data", Journal of Magnetic Resonance, 1998, 132, pp. 65-77.
Butler, J. P. et al., "Estimating Solutions of First Kind Integral Equations with Nonnegative Constraints and Optimal Smoothing", SIAM Journal of Numerical Analysis, 1981, 18(3), pp. 381-397.
De J. Cano, F. et al., "Magnetic resonance imaging of 1H, 23Na, and 35Cl penetration in Portland cement mortar", Cement and Concrete Research, 2002, 32, pp. 1067-1070.
Carr, H. Y. et al, "Effects of Diffusion on Free Precession in Nuclear Magnetic Resonance Experiments", Physical Review, 9, 1954, 13 pages.
Chandrasekera, T.C. et al., "Numerical inversion methods for recovering negative amplitudes in two-dimensional nuclear magnetic resonance relaxation-time correlations" Physical Review E, 2018, 98, 043308, 19 pages.
Chandrasekera, T. C., et al., "Rapid encoding of T1 with spectral resolution in n-dimensional relaxation correlations", Journal of Magnetic Resonance, 2008, 194, pp. 156-161.
Chen, Q. et al., "The internal magnetic field distribution, and single exponential magnetic resonance free induction decay, in rocks", Journal of Magnetic Resonance, 2005, 175, pp. 300-308.
Fordham, E. J. et al., "What are, and what are not, Inverse Laplace transforms" Diffusion Fundamentals, 2017, vol. 29, 8 pages.
Hahn, E. L., "Nuclear Induction Due to Free Larmor Precession", Physical Review, 1950, 77, 4 pages.
Hopper, T. et al., "Low-frequency NMR with a non-resonant circuit", Journal of Magnetic Resonance, 2011, 210, pp. 69-74.
Hoult, D. I., "Fast Recovery with a conventional probe", Journal of Magnetic Resonance, 1984, 57, pp. 394-403.
Hurlimann, M. D. et al., "Spin Dynamics of Carr-Purcell-Meiboom-Gill-like Sequences in Grossly Inhomogenous B0 and B1 Fields and Application to NMR Well Logging" Journal of Magnetic Resoanance, 2000, 143, pp. 120-135.
Hutchison, J. M. S. et al., "A whole-body NMR imaging machine", Journal of Physics E: Scientific Instruments, 1980, 13, pp. 947-955.
Hwang, F. et al., "Automatic Probe Tuning and Matching", Magnetic Resononance in Medicine, 1998, 39(2), pp. 214-222.
Li, S. et al., "A novel NMR instrument for real time drilling fluid analysis" Microporous Mesoporous Materials, 2018, 269, pp. 138-141.
Mandal, S. et al.,"An ultra-broadband low-frequency magnetic resonance system" Journal of Magnetic Resonance, 2014, 242, pp. 113-125.
McDonald, P. J., "Stray field magnetic resonance imaging", Progress in Nuclear Magnetic Resonance Spectroscopy, 1997, 30, pp. 69-99.
Meiboom, S. et al., "Modified Spin-Echo Method for Measuring Nuclear Relaxation Times", Review of Scientific Instruments 29, 1958, pp. 688-691.

* cited by examiner

DIGITAL RETORT MEASUREMENT SYSTEMS AND METHODS

CROSS-REFERENCE TO RELATED APPLICATIONS

The present application is a national stage entry under 35 U.S.C. 371 of International Application No. PCT/US2020/056747, filed Oct. 22, 2020, which claims priority to and the benefit of U.S. Patent Application No. 62/924,510, filed Oct. 22, 2019, the disclosure of which is incorporated herein by this reference in its entirety.

BACKGROUND

When building a well for the production of hydrocarbons such as oil and gas, drilling fluid is often circulated through the well for a variety of purposes. One function of the drilling fluid (also known as drilling mud) includes providing hydrostatic pressure. The hydrostatic pressure can be used to restrict or even prevent formation fluids from entering into the wellbore, to inhibit wellbore collapse or otherwise maintain wellbore integrity and stability, and to limit the effect of pressure spikes and prevent blowouts. Another function of the drilling fluid includes keeping the drill bit cutting elements cooled and lubricated during drilling, and to flush the cuttings away from the drill bit to avoid packing and balling of cuttings on the drill bit, which would reduce drilling efficiency.

The drilling fluid also serves as a mechanism for solids transport. In addition to flushing cuttings from the drill bit, the cuttings can be suspended in the drilling fluid. This can limit the sag of the cuttings toward the drill bit when drilling or fluid circulation is paused or stopped but can also be used to carry the cuttings to surface during the drilling operation. Various other functions of the drilling fluid include the transmission of hydraulic energy to downhole tools (e.g., mud motors), minimizing the impact of a drilling operation on the environment, and facilitating formation evaluation operations.

To balance these various functions of the drilling fluid, there are various general types of drilling fluids, and complex combinations of components within any particular drilling fluid. Significant resources can be expended to determine the particular formulation to use based on factors such as the formation being drilled, the depth, the type of drilling operation, the types of drilling tools, and the like. Some general categories of drilling fluids include water-based drilling fluids, oil-based drilling fluids, and synthetic-based fluids. With these drilling fluids, polymers, clays, chemicals, or other materials may be used as additives to obtain desired properties.

During a drilling operation, additional materials from the wellbore—including oil, water, or other fluids—may combine with the drilling fluid. The composition of the drilling fluid may therefore change over time, including the amount of water, the amount of oil, and the amount of solids within the drilling fluid. These changes can affect the properties of the drilling fluid, therefore changing the hydrostatic pressure provided by the fluid, the flowability of the fluid, the solids transport capabilities of the fluid, the ability of the fluid to seal a porous formation, and the like.

SUMMARY

Some embodiments of the present disclosure relate to methods of determining volumes fractions of a drilling fluid. For instance, volume fractions of any or all of oil, water, or solids may be determined. The methods include applying a magnetic field to a sample and measuring relaxation times of the magnetic response to the applied magnetic field. In some embodiments, a concentration of iron or other ferromagnetic material in the sample determined.

Some embodiments of the present disclosure relate to NMR devices to determine the oil, water, and solids volumes ratios of a drilling fluid. The NMR device may be an in-line device that receives drilling fluid returning from a wellbore and automatically evaluates the returned drilling fluid for oil, water, and solids volumes ratios. In some embodiments, the NMR device may raise a flag when iron accumulation is detected.

This summary is provided to introduce a selection of concepts that are further described below in the detailed description. This summary is not intended to identify key or essential features of the claimed subject matter, nor is it intended to be used as an aid in limiting the scope of the claimed subject matter.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims or may be learned by the practice of such embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIGS. 5-1 to 5-5 are $T_1$-$T_2$ correlation plots obtained using NMR techniques on various drilling fluid samples, including synthetic-based mud, oil-based mud, and direct-emulsion muds, according to embodiments of the present disclosure;

FIGS. 10-1 and 10-2 are charts illustrating raw NMR signals obtained from a $T_1$-$T_2$ measurement of a drilling fluid without and with iron contamination, respectively, according to an embodiment of the present disclosure.

FIGS. 11-1 and 11-2 are $T_1$-$T_2$ correlation plots obtained by inverting the raw NMR data of FIGS. 10-1 and 10-2, respectively.

FIGS. 12-1 and 12-2 are schematic illustrations of a partially unassembled NMR magnet and probe and an assembled NMR magnet and probe, respectively, according to embodiments of the present disclosure.

FIGS. 16-1 and 16-2 are schematic illustrations of respective pulse sequences for an inversion recovery measurement of $T_1$ and CPMG for a measurement of $T_2$;

FIGS. 17-1 and 17-2 are respective plots of raw echo amplitudes as recorded from a CPMG measurement and of projected zero-time amplitudes depending on the number of echoes used in the fit, according to embodiments of the present disclosure;

FIGS. 18-1 and 18-2 are respective plots of $T_1$-$T_2$ correlation of a drilling fluid before and after removal of low-level features and unphysical artifacts, according to embodiments of the present disclosure;

DETAILED DESCRIPTION

Figure 1:
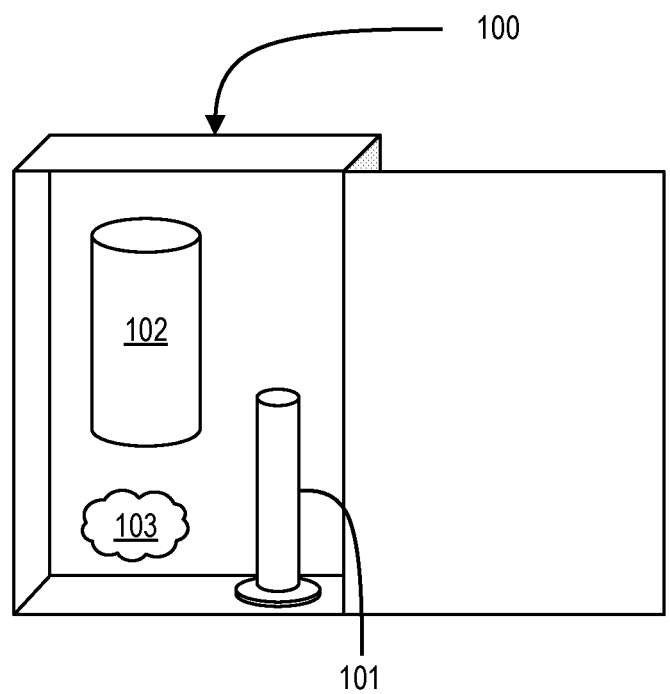
FIG. 1 is schematic view of an example digital retort instrument for measuring oil, water, and solids ratios of drilling fluid, according to an embodiment of the present disclosure.

Embodiments of the present disclosure relate to retort measurements. More particular embodiments of the present disclosure relate to measuring the oil, water, and solids content of drilling fluid. In some embodiments, nuclear magnetic resonance (NMR) is used to determine the oil, water, and solids content of drilling fluid by measuring magnetic response of a sample of the drilling fluid to an applied magnetic field. Example methods may be used on drilling fluid through in-line, automated monitoring of drilling fluid.

Control of drilling fluid formulation at the rig site during well construction can be a significant factor in successful job completion. An example formulation property that may be desirable to maintain includes the solids content and ratio to liquid content. Some solids, such as barite (a weighting agent) and clay (a rheology control) are added intentionally. Other solids, however, can accumulate during operations rather than as an intentional additive to the drilling fluid. For instance, low gravity solids (LGS) can enter the drilling fluid from the surrounding formation and accumulate during drilling and can lead to flow problems and stuck tools in the extreme case.

Other properties that can be monitored include the ratio of liquid components, such as oil and water fractions in oil-based muds (OBM) and synthetic oil-based muds (SBM) where an emulsified phase is water, or direct emulsion muds (DEM) where the emulsified phase is oil. The oil, water, and solids (OWS) volume fractions in a drilling fluid can be determined in spot checks by a mud engineer using a manual retort instrument 100 such as that shown schematically in FIG. 1. The retort instrument 100 measures a sample of drilling fluid (e.g., 50 ml volume) that is loaded into a crucible and weighed to determine the drilling fluid density. The sample is heated through a manual heating process or by setting an electronic temperature controller. To determine the OWS, the liquid fractions (oil and water) boil and leave behind the solids. The boiling of the liquid fractions breaks the emulsion. The liquid vapor is condensed into a volumetric measuring cylinder 101 to separate the liquid fractions, and the amount of each liquid phase present is determined by eye. The mass of the solids remaining in the crucible is also measured. The lime and salt (e.g., calcium chloride and sodium chloride) contents can be obtained in separate chemical titration analyses. The determined OWS, drilling fluid density, lime concentration, and brine salt content can each be stored (e.g., in a spreadsheet or other data structure) and used to calculate a ratio of high gravity solids (HGS) to LGS ratio.

The type of retort measurement performed using the retort instrument 100 is a manual process that takes several hours per measurement. The process is also prone to errors, which can approach ±5% on volume fractions. Such errors can be introduced in any number of manners. For instance, visual inspection of volume fractions may be inaccurate, or equipment may not be fully cleaned or dry. For instance, a standard workflow for using the retort instrument 100 may include initially visually inspecting the cell body for any defects or indications of leaking. A condenser 102 may include an O-ring seal which can be checked and replaced.

The mud density may be obtained and the retort instrument 100 and the condenser 102 can be inspected to ensure they are clean and dry. The body of the retort instrument 100 can then be packed (e.g., with steel wool 103). Using a dropper, a quantity (e.g., 20 ml, 50 ml, etc.) of drilling fluid may be placed in a cup/crucible on an analytical balance and weighed. The body, cup, and condenser 102 may then be hand-tightened, and the retort instrument 100 may be placed in a heating jacket, while a J-tube is positioned under an outlet of the condenser 102. The heating cycle then begins. Following the cycle, the J-tube can be removed and allowed to cool to ambient temperature. The retort assembly can also be removed and cooled, with the cooling possibly being aided (e.g., by a fan). The total solids, water, and oil volumes in the J-tube can be manually and visually determined and recorded. Such a process includes multiple inspections, and if inspection does not occur or is improperly performed, errors can be introduced. The results thus also depend on the operator. Additionally, as the process occurs over 2 to 3 hours, rapid measurements in real-time as well as near-continuous measurements do not occur. Other testing procedures, including titration for chlorine content of brine (performed separately), can also be imprecise and/or unreliable.

Such a retort measurement is also not easy to automate for continuous online monitoring of the mud properties. This is for a variety of reasons, including the difficulty of installing and using automation equipment at a wellsite, as well as due to the hours taken to obtain the measurement. Manual instruments currently available are also not particularly amenable to automation and are not easily made Atmospheres Explosible (ATEX) compliant. There is also an inherent health and safety risk associated with boiling flammable organic materials (e.g., diesel).

Therefore, an alternative digital measurement technology that can determine the OWS in a few minutes and in a flow line configuration could be a valuable tool to the mud engineer. Such measurements could integrate directly with a digital architecture to also enable automated remedial treatment of drilling fluids at the rig site to maintain drilling operation efficiency and reduce the risk of chronic failure modes, such as stuck pipe.

Figure 2:
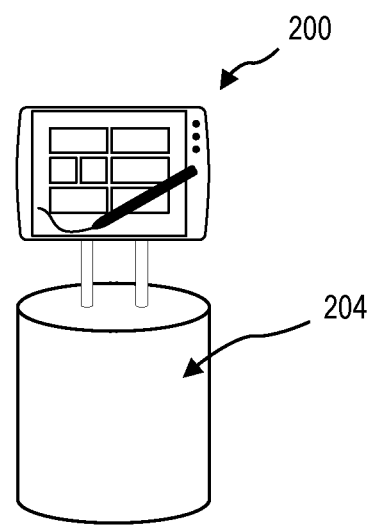
FIG. 2 is schematic view of a capacitance meter immersed drilling fluid.

For instance, an example process for obtaining a retort measurement is shown in FIG. 2. This process uses a capacitance meter 200 immersed in a container of drilling fluid 204. The capacitance meter 200 determines OWS by repeated measurements of the drilling fluid 204 under differing conditions. For instance, the drilling fluid 204 may be diluted with a liquid to provide different reference points. The capacitance meter 200 can also measure the brine salinity of the drilling fluid 204.

The capacitance meter 200 may be particularly useful as an alternative to the retort instrument 100 of FIG. 1 for oil-based fluids. The system does, however, mix liquids in a manner that is difficult to automate and make ATEX compliant, and thus is difficult to use as an in-line measurement. Further capacitance measurements have only been shown to be of particular use to OBM and lack accuracy for DEM or WBM. There are also concerns about the measurements made in the presence of iron contamination.

One technology that is amenable to automation of OWS measurements is NMR. An example embodiment of an NMR instrument includes a strong permanent magnet, a tuned radio frequency (RF) probe (solenoid), a spectrometer, an RF power amplifier, and an external PC for experimental control plus data processing and storage. The NMR instrument uses RF electronics to detect the signature of nuclear spin precession in a magnetic field. In an example embodiment, a low field (e.g., $B_0$=100 mT) magnet is used and $^1$H nuclei (protons) are detected at a resonant frequency of $f_0$=4.2 MHz. The spins are manipulated using a series of RF pulses (known as a pulse sequence), and the time for the spins to return to equilibrium (relaxation time) can be used to identify the liquid components. As the detected signal is proportional to the number of resonant nuclei in the sample, the signal amplitude can be scaled to liquid volume. If the total sample volume is known, then the solids content (which provide no NMR signal) is determined by subtraction of the total liquid volume. In this way, the OWS volume fractions are determined completely by the NMR instrument. A combination of longitudinal ($T_1$) and transverse ($T_2$) relaxation times are measured in a two-dimensional (2D) correlated experiment. These relaxation time measurements are interpreted automatically to provide a digital record of the OWS values that are stored electronically or transmitted elsewhere for further analysis. The automated interpretation and combination of NMR with other measurement technologies in a single unit can enable robust and reliable results.

Figure 3:
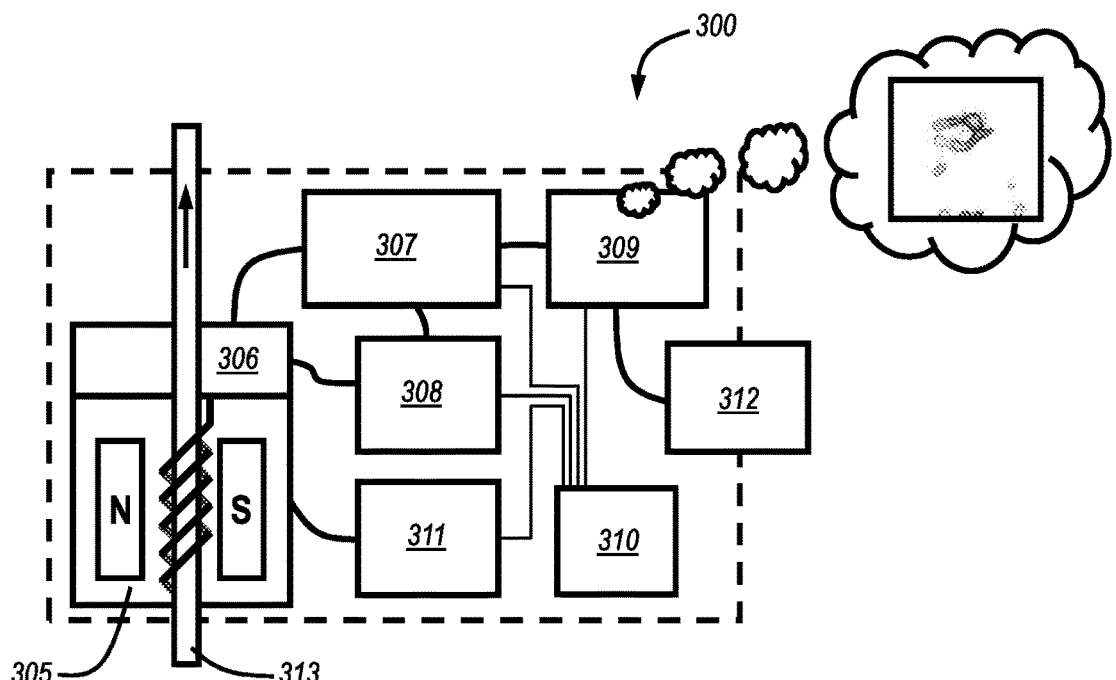
FIG. 3 is a schematic view of a digital retort instrument and system for measuring oil, water, and solids ratios of drilling fluid, according to an embodiment of the present disclosure.

A schematic illustration of an example NMR digital retort tool 300 is illustrated in FIG. 3. As shown in FIG. 3, the illustrative tool 300 can include various components, such as an NMR magnet 305, an RF probe 306, a spectrometer 307, a power amplifier 308, an embedded computer or processor 309, an internal power supply 310, and a magnet heater 311 or other temperature control system.

The various components shown in FIG. 3 are illustrative and can also take any number of forms. For instance, for a highly portable system (possibly to be incorporated into other in-line mud rheology equipment such as the RHEO-PROFILER™ mud rheology system of M-I L.L.C. in Houston, Texas), the digital retort tool 300 may be designed and manufactured to have a low mass for portability and potentially a low cost for wide spread implementation in the field. For such a tool, the NMR magnet 305 may be a low-field NMR magnet and may have a mass of less than 4 kg or less than 2 kg. In one example, the NMR magnet 305 may be a cylindrical Halbach array; however, in other embodiments, a planar pole-piece magnet may be used as it is easier to reliably manufacture and less expensive to produce. While high precision NMR instruments may include very high-power magnets for heavier elements and higher resolutions, a low-field magnet can provide sufficient field strength for measurements of $^1$H nuclei.

The RF probe 306 may similarly be a miniaturized probe and, in some embodiments, may be an active damping feedback pre-amplifier (ADFP). The spectrometer 307 may include one or more boards. In some embodiments, the spectrometer 307 is a single board NMR spectrometer based on a fully programmable gate array (FPGA) chipset, and the power amplifier 308 may be or include a low power (e.g., up to 5 W, 10 W, or 15 W) RF power amplifier. The embedded computer or processor 309 may be used as a data acquisition and processing device and may run control and interpretation hardware or software using methods and techniques described herein.

The power supply 310 may provide internal power distribution and optionally electronic noise filtering. In some embodiments, the noise filtering is provided by a separate filter. In an example embodiment, the power supply 310 includes a linear AC to DC converter with multiple rails (e.g., 24 V rails) available to drive each component of the retort tool 300. The magnet heater 311 may operate as a temperature control system that regulates the operating temperature of the magnet to at least partially compensate for the wide variations in temperatures and conditions experienced in the field.

A user interface 312 may be provided to interact with the retort tool 300. The user interface 312 may be fully or partially on the interior of the retort tool 300 (with the dashed line representing the body of the retort tool 300) or exterior of the retort tool 300. In some embodiments, the user interface 312 is an output. In other embodiments, the user interface 312 is an input. The user interface 312 may also provide both input and output capabilities. For instance, the user interface 312 may include a touch screen.

Figure 4:
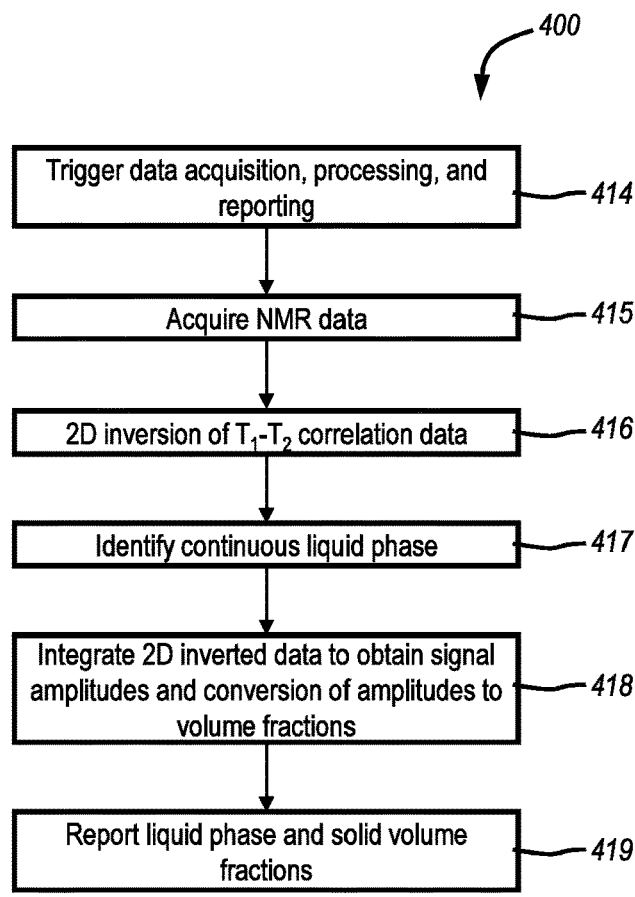
FIG. 4 illustrates an example method for measuring oil, water, and solids content of a fluid, according to embodiments of the present disclosure.

To describe how interpretation of NMR data obtained by the with the digital retort tool 300 can be automated, an example flowchart of a digital retort method 400 is shown in FIG. 4. In the method 400, one or more of data acquisition, processing, or reporting can be triggered at 414. Triggering the method 400 at 414 may be performed in any suitable manner. For instance, using the user interface 312, a "go", "start", or similar command may be initiated. In other embodiments, an automated flag may trigger the method. For instance, the processor 309 may schedule a data acquisition process to initiate periodically (e.g., every 30 minutes, every 45 minutes, every hour, every 2 hours, etc.). Thus, the trigger at 414 may be a manual input or a digital input/flag.

When the process is triggered at 414, NMR data can be acquired at 415. Using the example retort tool 300 of FIG. 4, this may include flowing drilling fluid into the retort tool 300 using a flow line 313. The flow line 313 may pass into or through the NMR magnet 305. The flow line 313 may form a continuous flow line and drilling fluid may flow through the flow line 313 while NMR data is acquired. In other embodiments, the flow line 313 may allow drilling fluid to flow into the retort tool 300 where it is contained and stops flowing while NMR data is acquired. Following acquisition of the NMR data, the analysed fluid may flow out of the flow line 313.

The NMR data that is acquired at 415 may include $T_1$-$T_2$ correlation data. The method 400 may also include performing a 2D inversion of the $T_1$-$T_2$ correlation data at 416. In some embodiments, this includes setting parameter ranges, selecting smoothing parameters, and terminating a non-linear solver. Optionally, these parameters, parameter ranges, or terminations may be performed manually (e.g., using user interface 312), or may be performed automatically (e.g., as initiated by execution of computer-executable instructions by the processor 309). The continuous liquid phase may then be identified at 417 using an appropriate method. For instance, the maximum peak amplitude may be used. In the same or other embodiments, machining learning or forward modelling may be applied to determine the continuous liquid phase.

The 2D inverted data obtained at 416 may also be integrated at 418. Such integration of the 2D inverted data can be used to obtain amplitudes of one or more peaks and/or the entire spectrum. Those amplitudes can then be converted to volume fractions. Thereafter, continuous and discontinuous (emulsion) liquid phases and solid volume fractions can be output at 419.

While determining OWS can be accomplished based on the 2D inversion performed at 416, this does not prevent other methods of the present disclosure from performing other inversions. For instance, oil-water ratio (OWR) measurements may be performed using one-dimensional $T_1$ or $T_2$ distributions, or the ratio of $T_1/T_2$ as a 1D diagonal projection of a 2D $T_1$-$T_2$ correlation plot. However, such other distributions may not be as robust for some analysis and may lead to overlap for different fluid phases in some conditions.

The method 400 may also include other actions or steps, and the retort tool 300 may include further programming or features to implement other actions or processes. For instance, in some embodiments, the retort tool 300 can perform automatic quality control checks (optionally implemented within method 400). For instance, the RF pulse amplitude may be measured to ensure the power amplifier 308 is functioning within specifications. This may be done, for instance, using a search coil. In another embodiment, the retort tool may detect when a sample is present, which can trigger data acquisition at 414. Further, RF probe sensitivity may be monitored by, for instance, detecting a calibration RF pulse through the search coil. In still other embodiments, a magnetic susceptibility check may be performed based on free induction decay (FID) relaxation time $T_2^*$ to ensure acceptable levels of iron contamination. Thus, in some embodiments, the retort tool 300 monitors whether a sample has excessive iron contamination. Excessive iron can compromise the resolution and/or precision of the measured spectra, while, in some embodiments, iron concentration measurements can allow for some correction and/or data filtering of the measured spectra.

Still other quality control checks that may be performed manually or automatically by the retort tool 300 include monotonically increasing ($T_1$) or decreasing ($T_2$) signal amplitudes to avoid poor data, such as from memory errors, or monitoring to ensure acceptable signal-to-noise ratios.

In some embodiments, second NMR data is acquired from a second fluid sample by the same or a second digital retort tool. In some embodiments, the second fluid sample may be collected from a different source than the drilling fluid sample. In some examples, the first drilling fluid sample may be collected from drilling fluid entering the wellbore, and the second fluid sample may be collected from the drilling fluid exiting the wellbore. In other examples, the first drilling fluid sample may be collected from drilling fluid entering the wellbore, and the second fluid sample may be collected from the drilling fluid in the downhole environment, such as at or near the bit. The second NMR data and/or processed second NMR data can be compared to the NMR data from the first drilling fluid sample to evaluate changes in the drilling fluid and/or identify where changes in the drilling fluid are occurring.

The retort tool 300 may also be calibrated to ensure the determined OWS are within a desired tolerance for error. Calibration may be manual or automated; however, in an automated method, the initial setup may include calibration using RF pulse duration. Calibration may also include calibration of resonance frequency (e.g., from FID), and calibration of experimental parameters (e.g., based on single-shot $T_2$ measurement).

Samples of drilling fluid may be provided to the retort tool 300 manually or, as discussed herein, in an automated manner (e.g., using flow line 313). Example methods for automatically providing drilling fluid samples include using flow line(s) 313 and pump(s). Ditch magnets may be used to catch non-colloidal iron particles, and flow lines 313 may be flushed before NMR detection to ensure the sample chamber is clear of previous samples of drilling fluid.

Optional complementary measurement technology may be included with the retort tool 300, or connected thereto, and can include a flow line magnetic susceptibility meter to ensure iron is not accumulating in the magnet (compare NMR and external magnetic susceptibility values), to sample temperature, to sample density, or to determine salinity for brine (e.g., chlorine content, which could in some cases be achieved using NMR). Additional data such as fluid density and salt content can be combined with OWS obtained/provided at 419 of FIG. 4 to determine HGS and LGS ratio.

Additionally, in the example mentioned herein in which the present tool is incorporated with in-line mud rheology equipment, the NMR retort tool 300 may function along the existing tool that determines viscosity and density (Coriolis meter) to provide automatic logging of the drilling fluid properties during well construction, and can be deployed on the rig.

An NMR retort tool of the present disclosure is not, however, limited to use with another in-line mud rheology tool. In some embodiments, for instance, the NMR retort tool 300 can operate as a stand-alone instrument. The reduction in measurement time (e.g., 10-30 minutes vs 3 hours), the improved health and safety aspects (e.g., no boiling liquids), the technician-friendly interface (e.g., using automated operation), and improved accuracy provide particular benefits over a conventional retort tool.

While embodiments of the present disclosure relate to NMR measurements applied to drilling fluid, the same NMR magnet 305 and tool 300 could be applied to determine the petrophysical properties of drilled cuttings at the wellsite in order to determine features such as formation porosity and permeability. Some modifications could also be made for such a system, such as a reduction in magnetic field strength (e.g., to $B_0$=50 mT ($f_0$=2 MHz)), while ensuring the probe 306 has a suitable size (e.g., at least 20 to 25 mm), to increase applicability of the tool 300 to both drilling fluid and drill cuttings.

The retort tool 300 may provide information related to drilling fluid composition (or related to drill cuttings) to other tools or systems within a drilling system. For instance, a drill rig or well site may include an automated drilling mud remediation tool that, upon acquiring information from the retort tool 300, can determine any remedial actions to take on the drilling fluid during well construction. Other systems may include well planning or well drilling systems. Based on drilling fluid composition, a well planning system may alter a drill plan (e.g., change mud motor parameters based on fluid changes) or may alter a well drilling operation (e.g., change rotational speed, weight on bit).

Validation of the retort tool 300 and method 400 were performed in lab experiments using a benchtop NMR instrument in order to determine the achievable accuracy and precision on the OWS measurement and to evaluate potential difficulties associated with iron contamination. For such validation testing, fluid samples of controlled volume and mass that emulated field samples were tested.

To perform the NMR measurement, a drilling fluid sample of known/controlled volume and mass was placed in a 25 ml calibrated pycnometer made from borosilicate glass, and the pycnometer was placed in the NMR tool at ambient temperature and pressure conditions for the duration of the measurement. A benchtop magnet with a field strength of $B_0$=50 mT was used, which corresponded to a resonant frequency of $f_0$=2.4 MHz for $^1$H. The instrument was designed for rock core analysis, to emulate the behaviour of downhole logging tools, and was able to accommodate samples of approximately 50 ml (plus a high-temperature, high-pressure core holder). Pulse sequence implementation and data acquisition were performed on a DRX-TCP spectrometer. The RF pulses had durations of $t_{90}$=15 μs and $t_{180}$=30 μs for 90° and 180° tip angles, respectively. The signal-to-noise ratio (SNR) of the measurements was improved using an ADFP probe, and a single magnetic field gradient coil (vertical y-axis) was driven by a high-power audio amplifier. Gradient strengths up to $g_{max}$=50 G·cm$^{-1}$ were available but not used in this experiment.

For this laboratory test, $T_1$-$T_2$ relaxation time distributions were determined. The pulse sequence included an inversion recovery interval followed by a Carr-Purcell-Meiboom-Gill (CPMG) echo train. The $T_1$ recovery times were increased from $\tau_1$=100 μs to 3.0 s in 32 logarithmic intervals. $T_2$ relaxation times were measured with an echo spacing of $t_c$=100 μs and n=5000 echoes. Processing of the data was achieved with an existing numerical inversion method.

Free induction decays (FID) were determined using a standard pulse-acquire method. The decays were assumed to be exponential in the presence of the paramagnetic barite and were fitted with a single-exponential decay function to determine the $T_2^*$ relaxation time. The $T_2^*$ relaxation time was taken to be an indicator of the magnetic susceptibility contrast.

The total signal amplitudes for 25 ml of drilling fluid base oil (various synthetic low-viscosity oils) and brine (various salt concentrations) were determined by integrating over $T_1$-$T_2$ relaxation time distributions of these calibration samples. These signal amplitudes were used to calculate the hydrogen index (HI=number of detected hydrogen nuclei per unit volume) for water and base oil. The HI of oil was slightly higher by a factor ×1.05 (i.e., more signal was obtained from 1 ml of oil than from 1 ml of water). No significant difference was observed between the different synthetic base oils measured.

Various interpretation methods were explored to robustly extract the oil to water ratio (OWR) from the $T_1$-$T_2$ relaxation time distributions for a series of drilling fluid samples. The best results for this test were achieved by associating the largest peak in the 2D distribution with the continuous phase (e.g., oil in OBM) and associating the other peaks with the discontinuous phase (e.g., water in OBM).

Figures 1, 5:
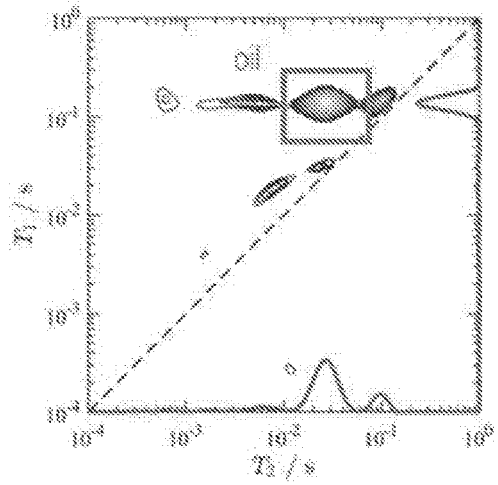
Figures 2, 5:
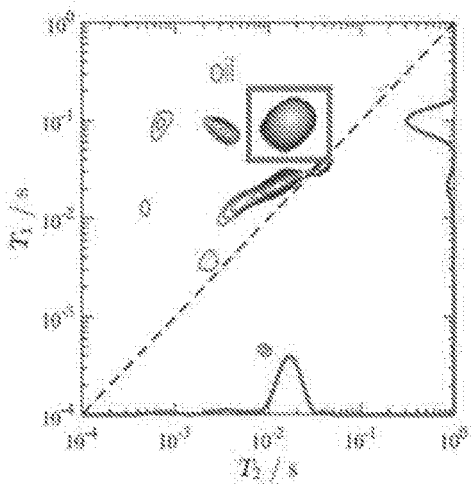
Figures 3, 5:
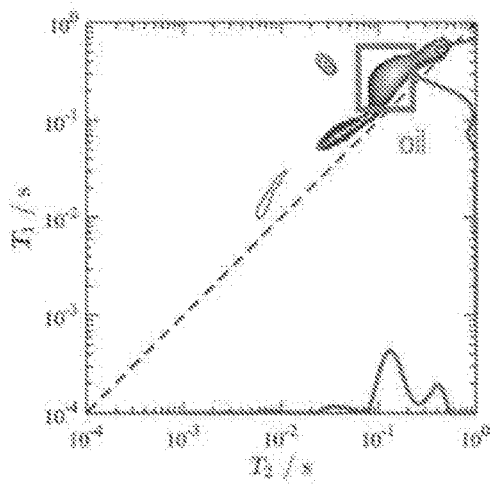
Figures 4, 5:
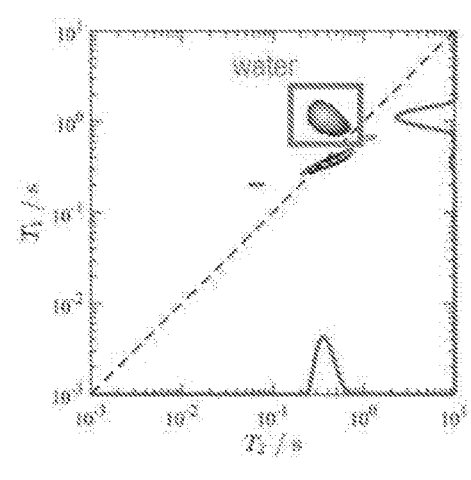
Figure 5:
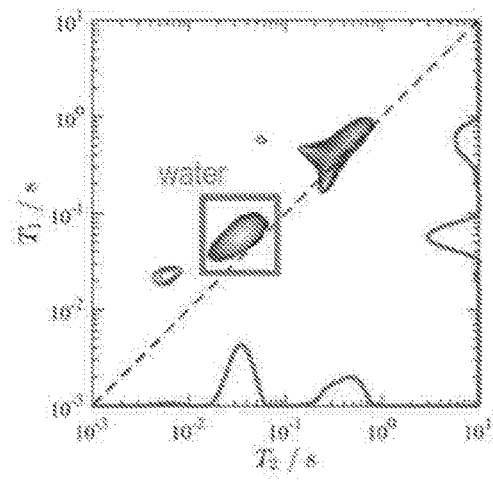

A selection of $T_1$-$T_2$ correlation plots obtained at 2 MHz for various field-equivalent drilling fluid samples are shown in FIG. 5 (which includes FIGS. 5-1 to 5-5). The selection includes a SBM in FIG. 5-1, OBM (diesel-based) in FIGS. 5-2 and 5-3, and DEM samples in FIGS. 5-4 and 5-5. A basic interpretation of OWR is achieved by associating the largest peak in each plot (in the box) with the continuous phase (either oil or water as labelled). The integral of the peaks provides the volume of the liquid components, and the integral over the entire 2D plot provides the total liquid volume (for solids volume fraction determination). In each plot, the dashed diagonal line shows $T_1$=$T_2$ and the marginal 1D projections (red lines along lower and right edges) are included for clarity.

It is clear from this selection by comparing FIGS. 5-2 and 5-3 that the 2D data plots are highly variable, even between supposedly identical muds, which are the same formulation before and after cleaning and dilution with base oil at the rig site. Similarly, FIGS. 5-4 and 5-5 are the same DEM formulation at the start and end of a drilling operation. Some of the proliferation of peaks arises from the influence of the paramagnetic barite (the diffusion contribution to $T_2$ results in the recognized dual peaks of the spectra), and it is expected that sufficient samples will allow association of the peaks with various detailed formulation components (e.g., surfactants, dispersants, polymers, etc.). The goal of this experiment was to separate the continuous and discontinuous volume fractions, which was achieved using the interpretation method illustrated in FIG. 5. It is also worth noting that for these fluids, the same OWR information cannot be extracted from either of the 1D $T_1$ or $T_2$ marginal distributions (included in red along the edges of the plots) independently. Analysis of the full 2D correlation data set is required to robustly and uniquely determine the OWR.

Figure 6:
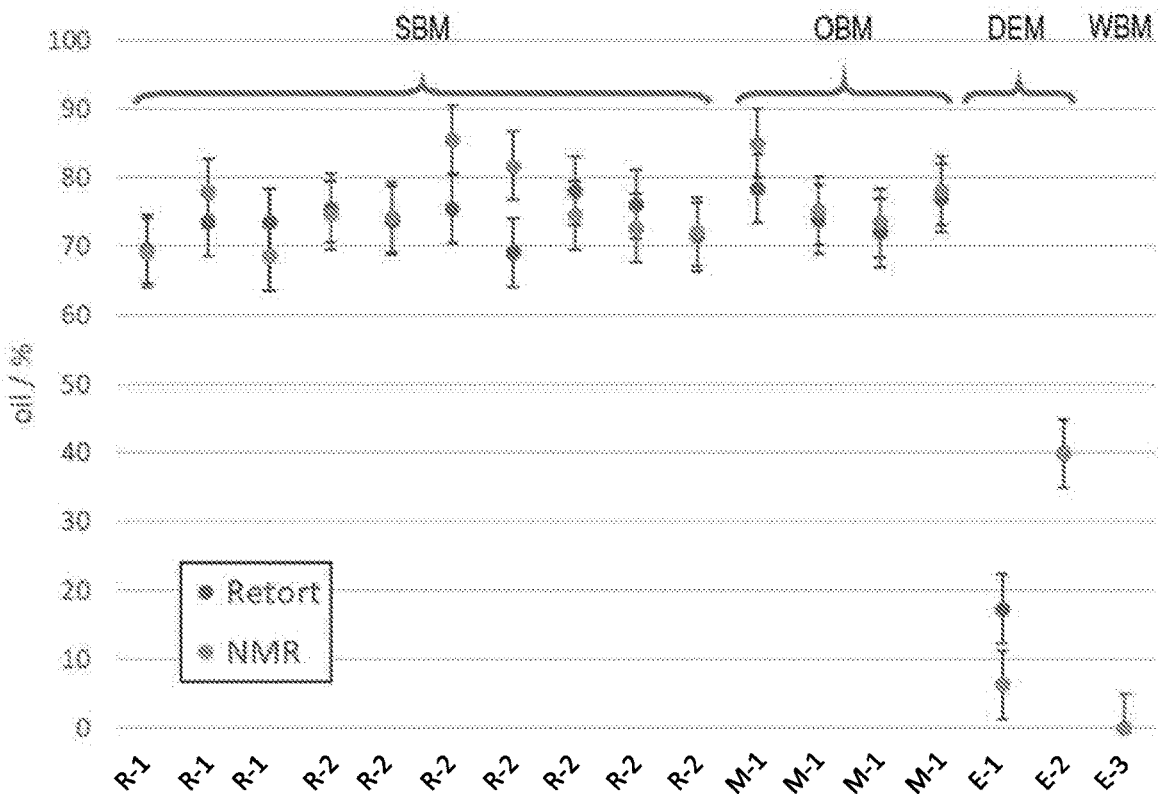
FIG. 6 is a chart illustrating oil volume fraction as a percentage of liquid volume for a range of drilling fluids, according to embodiments of the present disclosure.

FIG. 6 illustrates experimental data of oil volume fraction (expressed as % liquid volume) in a range of used drilling fluids. A comparison is made between the manual retort measurement (blue points, data supplied by mud engineers) and the NMR measurement of the same (orange points). The error bars indicate the ±5% precision on the manual retort measurement. When the two points lay within the error bars, the NMR and manual retort values are considered equivalent.

The combined OWR data for the selection of drilling fluid samples—obtained by manual retort and NMR analysis—are shown in FIG. 6. In most cases, and as shown by the error bars, the two oil fractions are within the accepted experimental error of the manual retort measurement. There are, however, some obvious outliers. The NMR measurement of one of the R-2 samples provides an exceptionally high oil volume fraction compared to the manual retort. That sample contained significant iron contamination and as such the 2D plot was over-smoothed (see FIG. 7), making separation of the oil and water signals challenging.

Figure 7:
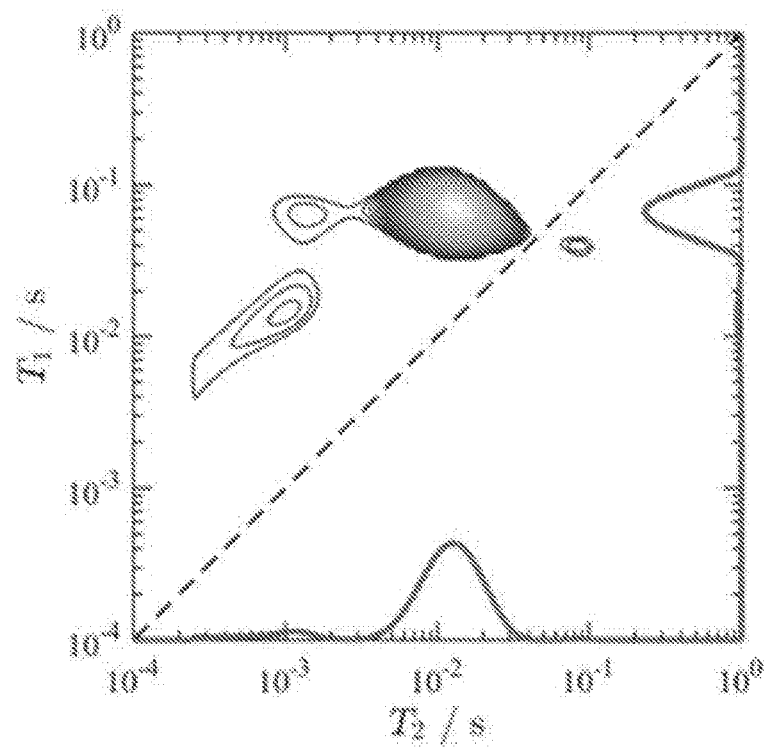
FIG. 7 is a chart showing an example $T_1$-$T_2$ distribution from a drilling fluid sample heavily contaminated with colloidal iron particles, according to an embodiment of the present disclosure.

FIG. 7 illustrates an example $T_1$-$T_2$ distribution from a drilling fluid sample heavily contaminated with colloidal iron particles. Note that the peaks are broadened, and it is difficult to uniquely identify the oil and water components (compare to the SBM sample with low iron contamination in FIG. 5-1). The dashed diagonal line indicates $T_1$=$T_2$ and the 1D marginal projections are included in red along the bottom and right edges.

Figure 8:
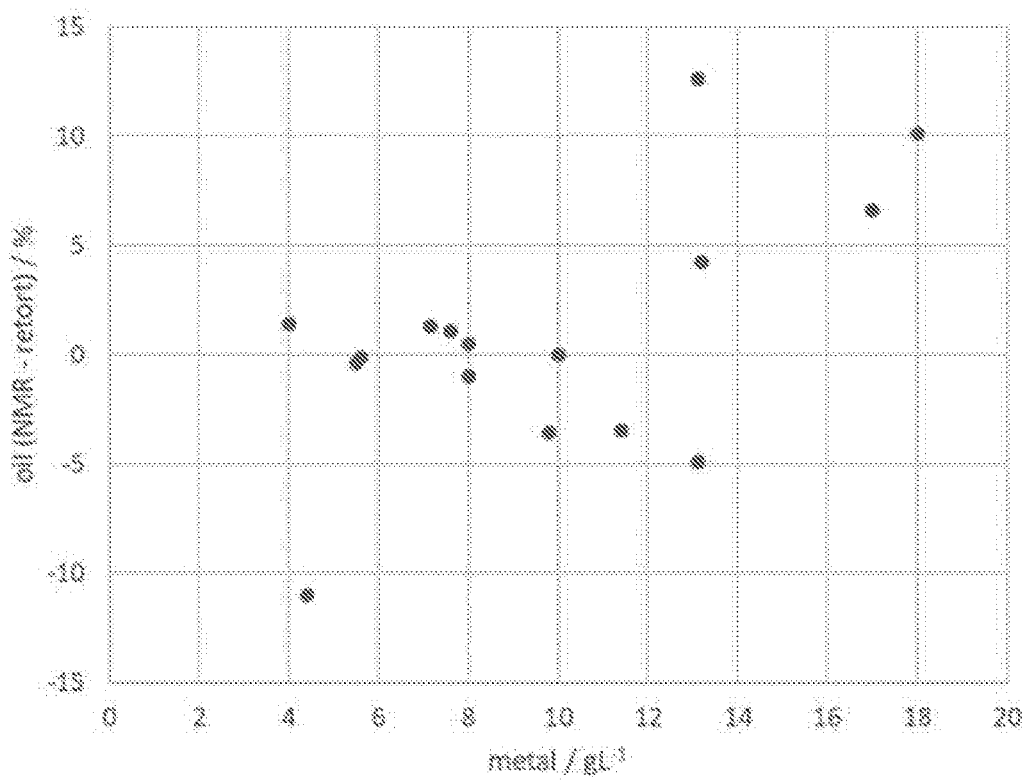
FIG. 8 is a chart illustrating iron per unit volume of drilling fluid extracted from drilling fluids, according to embodiments of the present disclosure.

The oil fraction for the E-1 sample in FIG. 6, corresponding to the $T_1$-$T_2$ distribution in FIG. 5-4, is underestimated for the same reason. In samples with negligible solids, the oil and water exhibit very similar relaxation times. The presence of some paramagnetic solids (e.g., barite) provides relaxation time contrast between the liquid phases, but too much iron contamination reduces the sensitivity of the NMR measurement. A more ideal R-1 SBM sample containing barite but minimal iron contamination (see first data point in FIG. 6) corresponding to the $T_1$-$T_2$ distribution in FIG. 5-1, provides excellent correspondence between the NMR measurement and the manual retort measurement. To reveal the sensitivity of the NMR measurement to iron contamination, the error (the difference between NMR and manual retort oil fractions) is plotted against ferrous iron content in FIG. 8. In FIG. 8, the metal loading was determined as the mass of ferrous iron per unit volume of drilling fluid extracted using a powerful magnet after breaking the emulsion. There is no obvious correlation between the measurement difference and the metal loading, except at very high metal loadings where the measurement difference is seen to abruptly increase.

In muds that are used in the field, the ferrous iron contamination is expected to arise from erosion of the steel drill string or casing. Large iron particles are typically removed at the surface by the shale shaker, and the iron that remains in the drilling fluid by the time it reaches an NMR instrument is in the form of particles of colloidal iron (e.g., <100 μm). The rheology of the drilling fluid may hold the colloidal iron in suspension, making it a challenge to remove by using ditch magnets on the flow line or other conventional techniques at the wellsite.

Figure 9:
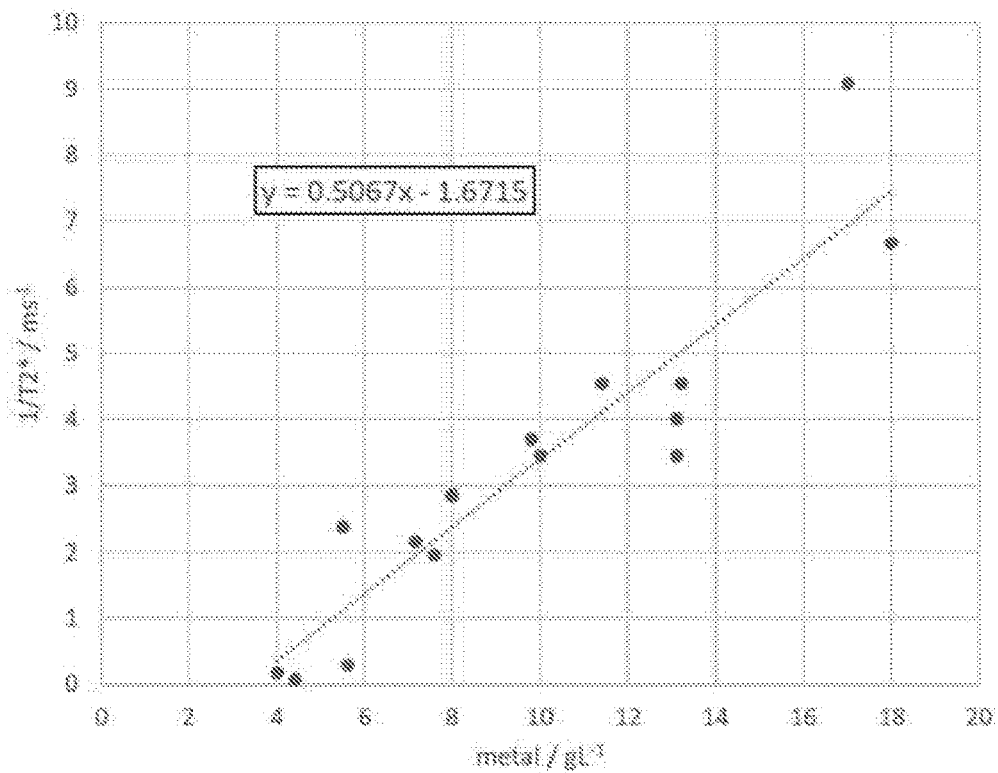
FIG. 9 is a chart plotting $T_2^*$ relaxation time as a function of ferrous iron content for drilling fluid samples, according to embodiments of the present disclosure.

To properly assess the influence of metal loading, the $T_2^*$ relaxation time (defined by local magnetic field distortions) was measured for the set of samples. In this case, a strong correlation was observed between the relaxation rate (inverse of time) and the ferrous metal loading. This can be observed in FIG. 9, where $T_2^*$ relaxation time is plotted as a function of ferrous iron content of the drilling fluids. The metal loading was determined as described relative to FIG. 8. As shown, the measurement of $1/T_2^*$ provides a "cut-off" at approximately 5 ms$^{-1}$ for "good" and "bad" samples. In drilling fluids without ferrous iron contamination, the $1/T_2^*$ relaxation rate was seen to correlate to the barite loading, as natural mined barite can frequently be contaminated with paramagnetic forms of iron oxide.

To better understand the effect of ferrous iron contamination on an NMR measurement, a control SBM formulation was prepared and dosed with colloidal magnetite powder, which is a ferrous form of iron oxide and a disruptive contaminate with regards to the NMR experiments performed. The colloidal magnetite powder has a very large magnetic susceptibility contrast to oil or water and was dosed up to 1 wt % of the fluid.

Figures 1, 10:
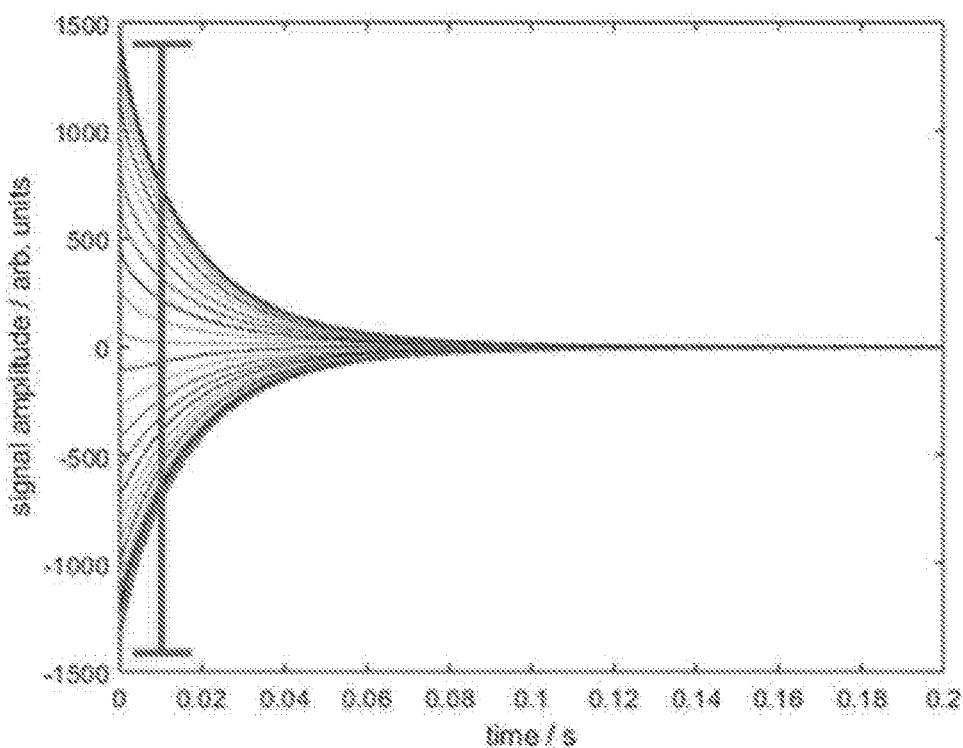
Figures 2, 10:
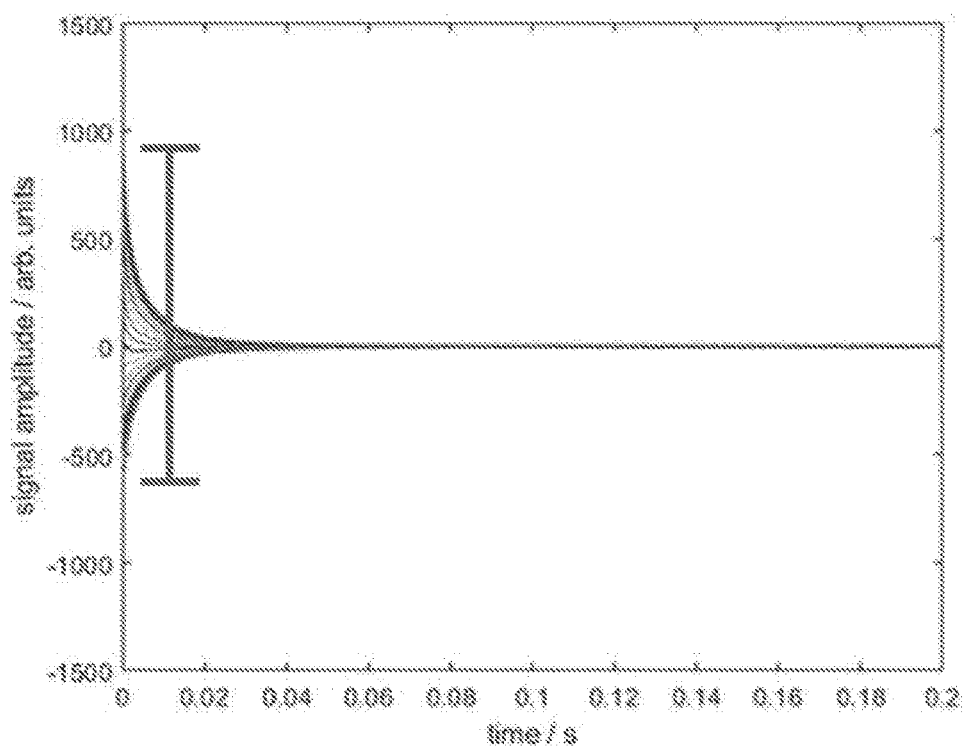

FIG. 10 (composed of FIGS. 10-1 and 10-2) illustrates raw NMR signals obtained from a $T_1$-$T_2$ measurement of an EMS 4740 SBM fluid with no ferrous iron contamination (FIG. 10-1) and with 0.6 wt % magnetite powder (FIG. 10-2). The red bar indicates the range of the data amplitude at zero time.

In the raw NMR signal decays obtained in $T_1$-$T_2$ correlation measurements of SBM drilling fluid with and without magnetite contamination as depicted in FIG. 10, each curve is a transverse relaxation decay and the different colored curves were obtained with different longitudinal recovery delays. The first and last signal amplitudes (as indicated by the red bars) should have equal magnitude but opposite sign. FIG. 10-2 shows, in the presence of significant ferrous iron contamination, the NMR signal is distorted. This appears to be due to imperfect RF pulses (asymmetric amplitudes at zero time, see red bar) and the transverse relaxation decay is notably faster due to the magnetic field distortion created by the iron particles. Corrections can be applied to restore the NMR signal amplitudes and decay rates; however, some of these corrections can be non-trivial and may rely on a detailed model of the magnetic fields. Quantitative OWS values can be obtained up to a loading of about 0.5 wt %, but above this level of ferrous iron contamination, the NMR measurements are compromised. In some embodiments, a measured ferrous iron contamination level above 0.5% can be used to correct the NMR measurements, as will be describe more herein.

Figures 1, 11:
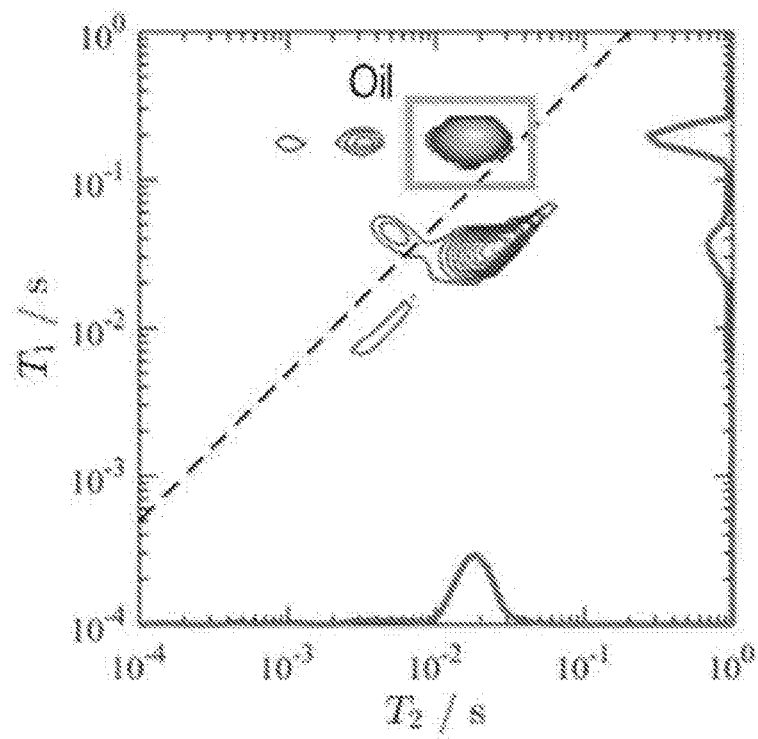
Figures 2, 11:
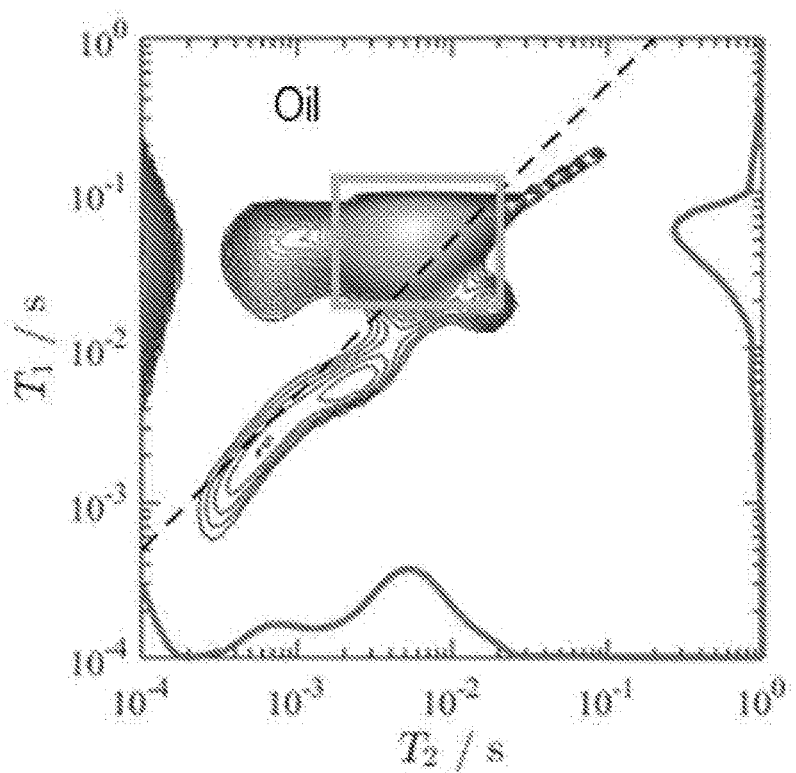

The $T_1$-$T_2$ correlation plots obtained by inverting the raw NMR data of FIG. 10 are shown in FIG. 11 (composed of FIGS. 11-1 and 11-2). FIG. 11-1 shows uncontaminated SBM and FIG. 11-2 shows SBM dosed with 0.6 wt % magnetite powder. In each plot, the dashed diagonal indicates $T_1$-$5T_2$ and the 1D marginal projections are shown in red along the bottom and right edges. The box indicates the region of the plot associated with the oil (continuous) liquid phase. In operation, it is expected that most of the ferrous iron particles surviving in the drilling fluid will be coated with a layer of paramagnetic hematite due to preferential surface oxidation. This may account for substantially higher resilience to iron contamination seen in used field muds as compared to samples artificially dosed with magnetite (compare FIG. 5 to FIG. 11-2).

Figures 1, 12:
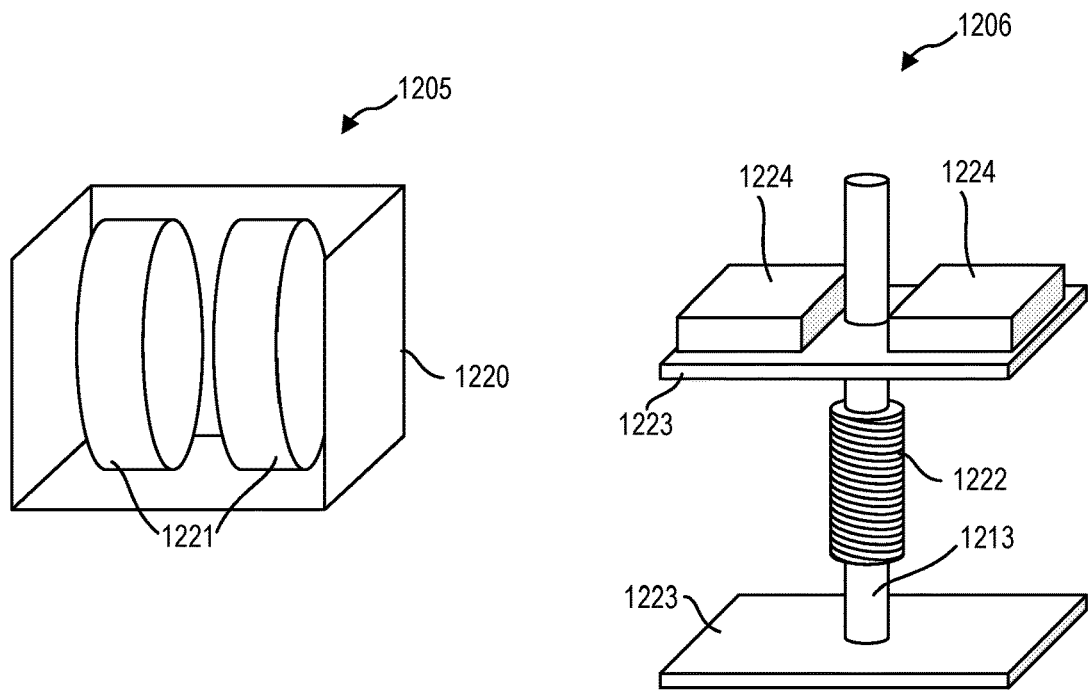
Figures 2, 12:
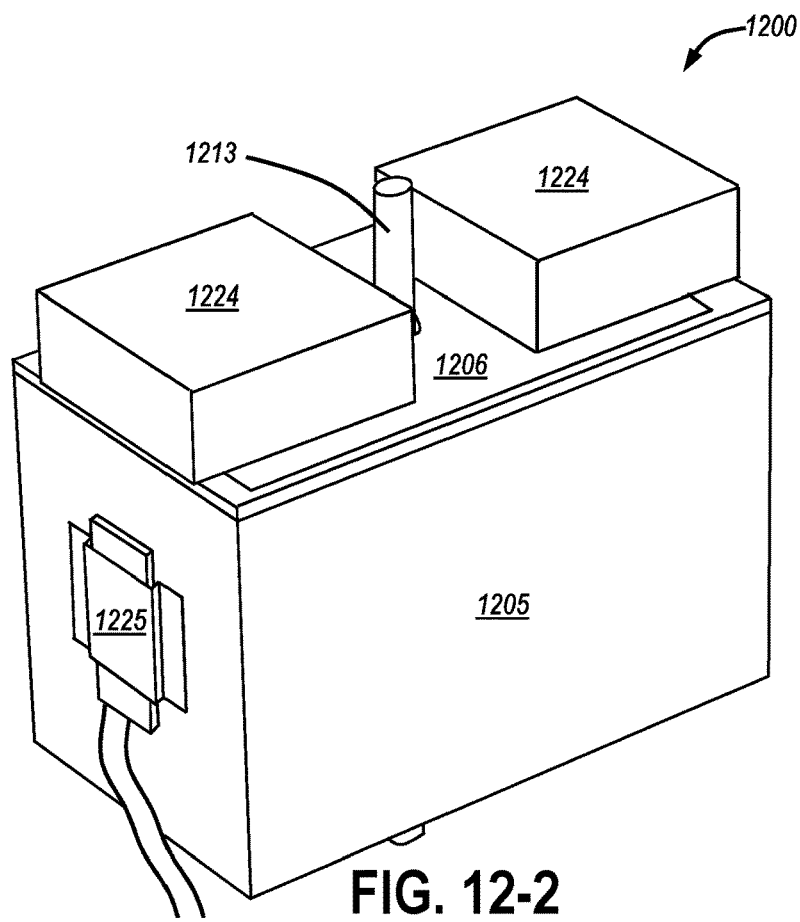

A further example of instrumentation that may be developed and which is generally consistent with that described with respect to FIG. 3 is shown in FIG. 12 (composed of FIGS. 12-1 and 12-2). Specifically, FIG. 12 is a schematic illustration of magnet 1205. FIG. 12-1 is a partially unassembled view in which the magnet 1205 is shown with two magnet lugs 1220 mounted in a body/yoke 1221 (e.g., steel, iron, etc.). In some examples, each magnet lug 1220 includes a disc of samarium cobalt (SmCo) rare earth magnet behind a soft iron or mild steel pole piece and an outer collar (which can improve field homogeneity in the pole gap), and a support bracket (e.g., steel, aluminum, etc.). The support bracket may be used to limit or prevent movement of the magnet lugs 1220 and thereby also restrict damage or dislodgement during transit or other movement.

FIG. 12-1 also illustrates an example probe 1206 that may be separable from the magnet 1205 and used in combination with the magnet 1205 (see assembly in FIG. 12-2). The probe 2106 may include an ADFP RF probe containing a resonator coil 1222 (e.g., copper solenoid wound on a PTFE former) with a flow line sample chamber 1213 inserted therein or coupled thereto. The coil 1222 can be positioned between top and bottom plates 1223 (e.g., formed from steel). When the probe 1203 is mounted in/on the yoke 1221 of the magnet 1205, the plates 1223 can be used to form an RF screen. The two boxes 1224 on top can contain pre-amplifier electronics. While the flow line sample chamber 1213 can be considered part of the probe, it may be a separable component in other embodiments. For instance, the sample chamber 1213 may be replaceable as necessary during routine servicing of the instrument and may be inserted into the probe 1206 either before or after the probe 1206 is mounted to the magnet 1205.

While the assembly that includes the magnet 1205 and probe 1206 may be any suitable size, some embodiments contemplate a miniature NMR assembly. In an example assembly, the magnet 1205 may have a size that is less than 2500 cm$^3$ or even less than 1500 cm$^3$, 1000 cm$^3$, 800 cm$^3$ or, 600 cm$^3$. For instance, the magnet 1205 may measure approximately 12 cm×8 cm×6 cm in one embodiment. The probe 1206 may have a corresponding size to fit into and on the magnet 1205 in the arrangement shown in FIG. 12. In such embodiments, the total weight of the assembly of FIG. 12 may be less than 10 kg, less than 5 kg, or even less than 2 kg.

In use, the NMR tool 1200 may be further enclosed (see dashed line of FIG. 3) in a suitable housing. For instance, tool may be enclosed within a thermal enclosure to allow the yoke 1221 to be maintained at a particular temperature or within a desired temperature range (e.g., 35° C.±0.1° C.). The strength of the magnetic field produced by a rare earth magnet may be inversely proportional to the magnet temperature and determined by the thermal coefficient of the material. SmCo, for instance, has a lower thermal coefficient than neodymium iron boron (NdFeB), another type of rare earth magnetic material. As a result, the strength of the magnetic field generated by a SmCo magnet is less sensitive to temperature changes; however, there may still be a desire to control the magnet temperature. To facilitate maintenance of the temperature, safe, self-regulating resistive panel heaters 1225 may be installed on the yoke 1221. Such heaters 1225 may be used, for instance, to heat the magnet 1205 to a super-ambient temperature. Temperature control may be achieved through a controller. An example controller may include the processor 309 of FIG. 3, or a separate controller, such as a supervisor board with proportional, integral, derivative (PID) software control, along with a power supply (which may be integral with or separate from the power supply 310 of FIG. 3).

The coil 1222 of the probe 1206 may act as an RF search coil and can perform various functions. For instance, the coil 1222 can detect RF pulses generated in the main resonator e.g., to ensure pulse power is maintained on long CPMG echo trains, which can be a limitation of lower cost RF amplifiers). Additionally, or in the alternative, the coil 1222 can provide an input signal to test the receiver circuit and sensitivity of the main resonator. The coil 1222 may therefore be used as a diagnostic tool in a fully automated embodiment of an NMR tool 1200.

Figure 13:
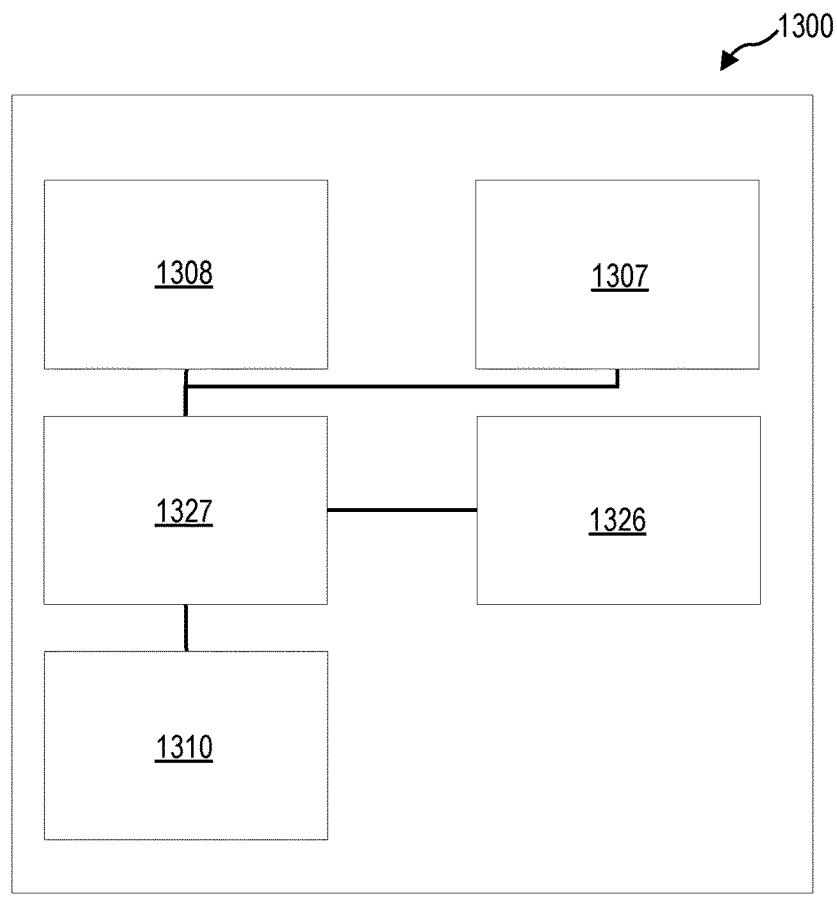
FIG. 13 is a schematic view of internal components of an electronics assembly that may be coupled to an NMR magnet and probe assembly such of FIG. 12, according to embodiments of the present disclosure.

FIG. 13 illustrates an example of the internal components of an electronics assembly 1300 that may accompany and be electrically coupled to an NMR magnet assembly such as that shown in FIG. 12. The electronics assembly 1300 may include various components, including components shown and described relative to FIG. 3. For instance, the electronics assembly 1300 may include a single-board spectrometer 1307, a supervisor board 1326 for temperature control, a power regulation and distribution board 1327, and a linear power supply 1310 that optionally includes multiple output rails. Such rails can illustratively operate between 5 V and 48 V. The electronics assembly 1300 may also include an RF amplifier module 1308, which optionally includes a heat sink.

In the example shown in FIG. 13, NMR experiments may be controlled by the spectrometer 1307, which is optionally based on a fully programmable gate array (FPGA) chip. The spectrometer board can generate the RF pulse sequence (following a pre-loaded instruction set) and perform the data acquisition. The board can include sufficient memory to store acquired data for transmission to an embedded or external processor for processing.

The RF amplifier used in the electronics assembly 1300 may use a suitable amount of power. For instance, 250 W output may be available; however, the RF probe (see probe 1206 of FIG. 12) may be effectively used with less power. Indeed, in some embodiments, the RF probe may be operated effectively with 10 W pulsed power. Thus, the RF amplifier 1308 may be a low power amplifier that operates at well below 250 W (e.g., 10 to 50 W).

The power supply 1310 may be suitably large to provide power to the other components, such as through multiple DC supply rails at various voltages. Optionally, the system can be powered entirely by a single rail (e.g., a single 24V rail) to reduce overall system cost and size, and to further simplify integration with other tools (e.g., a mud rheology instrument).

As discussed herein, a processor (e.g. processor 309 of FIG. 3) may be used to issue commands to the spectrometer 1307, store the acquired data, and perform data processing and automated interpretation. The processor may be a separate computing system (e.g., laptop computer, desktop computer, special purpose computer, programmable logic device, etc.). For instance, a separate computing device may run spectrometer software with a suitable application programming interface (API) and graphical user interface (GUI) such as that shown in FIG. 14. Such APIs, GUIs, and the like can be used on an external computing system or with an embedded processing system as contemplated herein. For instance, an integrated, embedded touch-screen user interface 1412 may use the GUI for user input and for output purposes. Embedded kits may use a Raspberry Pi or other similar embedded PC solution, although other more robust and powerful solutions may also be used.

Figure 14:
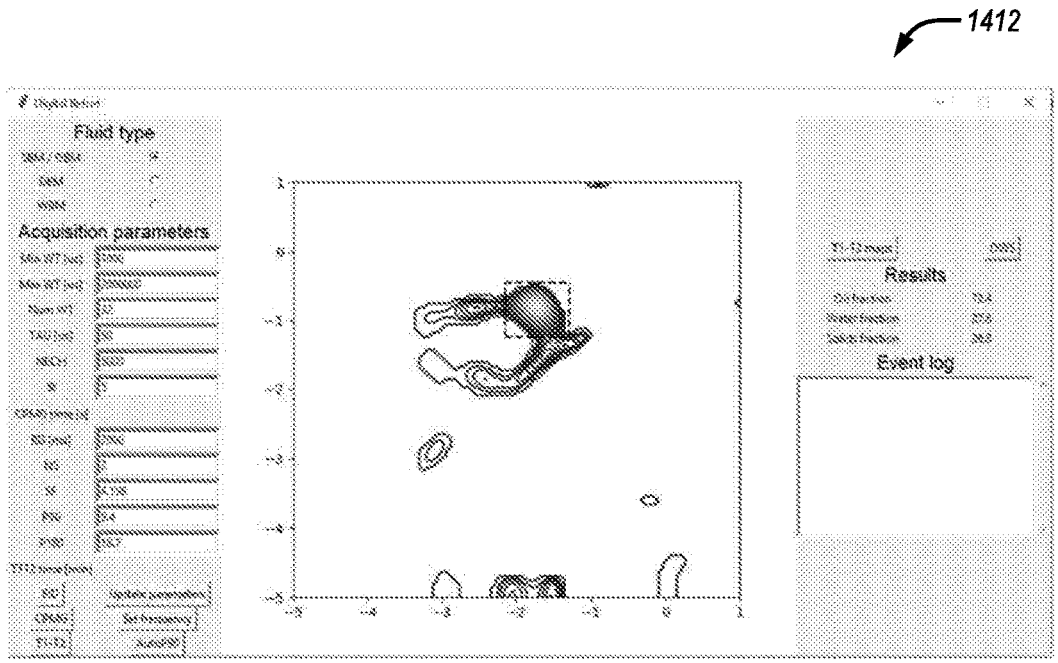
FIG. 14 is a view of a user interface of an NMR retort tool, according to embodiments of the present disclosure.

FIG. 14 is an example of a user interface 1412. In the illustrated embodiment, experimental parameters may be specified by the user, but these could also be pre-set or calibrated in real-time. The drilling fluid type can be selected, and experimental results can be presented. OWS values may then be reported. An event log may further be included to display the progress of measurements and any errors or problems that are identified by the software.

Figure 15:
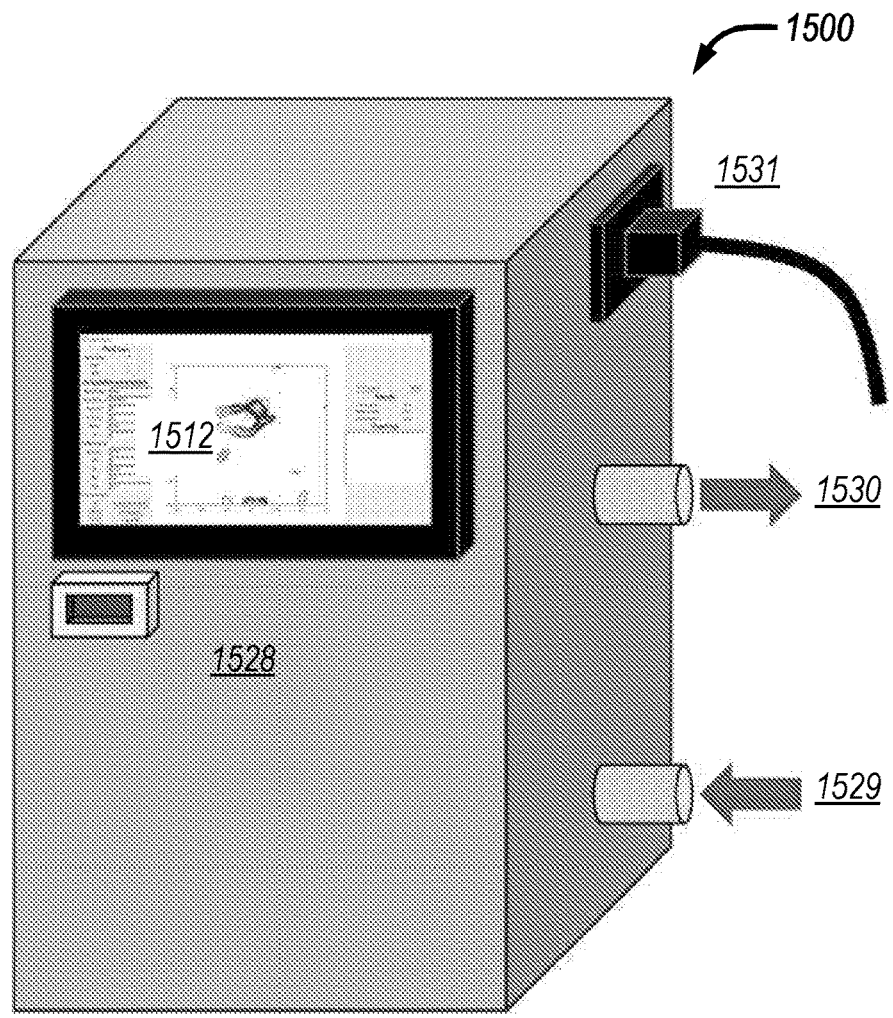
FIG. 15 is a perspective view of a self-contained digital NMR retort tool, according to embodiments of the present disclosure.

FIG. 15 schematically illustrates another concept of a standalone, digital retort instrument 1500 according to some embodiments of the present disclosure. In this embodiment, external user accessible components are visible, including a touch-screen user interface 1512. A data port 1528 (e.g., USB port, etc.) may be used for electronic data transfer. In flow line 1529 and out flow line 1530 may be provided to allow a sample to be loaded from an external source, e.g., a peristaltic pump. Main power may be provided via an electricity supply socket 1531.

In some embodiments, the flow line in which the sample is contained during measurements (not shown in FIG. 15) is optionally physically separate from the electronics such that the sample will not contact any electrical or heated components. This physical separation can allow the instrument to be made ATEX compliant. Some components that carry a risk of arcing—such as a RF probe electronics—may be isolated in order to comply with the regulations. Additionally, the section of the flow line passing through the magnet may be isolated (shut-in) and electrically grounded for the duration of the measurement. In some embodiments, such isolation may be implemented by actuated ball valves positioned just outside the yoke of the magnet. In some embodiments, the isolation is implemented by conductive non-magnetic fittings at the top and bottom of the bore to eliminate valves and potential clogs associated with the valves. This step can be used when measuring an electrically conductive fluid (e.g., DEM, WBM) because the flow line may act as an RF antenna and conduct interference (noise) into the probe.

When using the digital retort instrument 1500, the data can be acquired at a high rate (bandwidth), but the data rate can be reduced by a simple CIC filter stage before transmission to the processor. Other or additional filtering techniques may be used to further reduce the signal bandwidth, and can be implemented in software, firmware, hardware, or a combination thereof. Example filters use over-sampling methods employing finite impulse response (FIR) filters. On a low field system, contamination of the $^1H$ signal (4.19 MHz) by nearby $^{19}F$ resonance (3.94 MHz) can be eliminated in FIR filter design. Suitable filters can be constructed in a suitable programming environment (e.g., MATLAB programming environment available from MathWorks, USA which employs a built-in filter design toolbox). The filter coefficients can then be stored and transferred to for an end-use application.

During NMR data acquisition and processing, NMR pulse sequences can be applied to the drilling fluids. This may include any or each of "inversion recovery" for $T_1$ measurement, "FID" (also known as "pulse-acquire") for $T_2^*$ measurement, or "CPMG" for $T_2$ measurement. The inversion recovery and CPMG sequences can be appended to measure $T_1$-$T_2$ correlations.

Longitudinal recovery of the spin ensemble to equilibrium is governed by the exponential time constant $T_1$. The observed signal (magnetization) at time $\tau_1$ is described by:

$$\frac{M(t_1)}{M(0)} = 1 - 2\exp\left\{-\frac{\tau_1}{T_1}\right\}$$

Figures 1, 16:
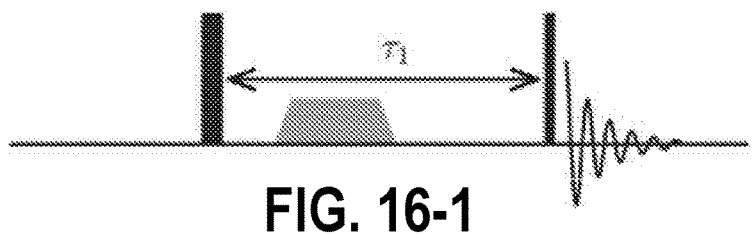
Figures 2, 16:
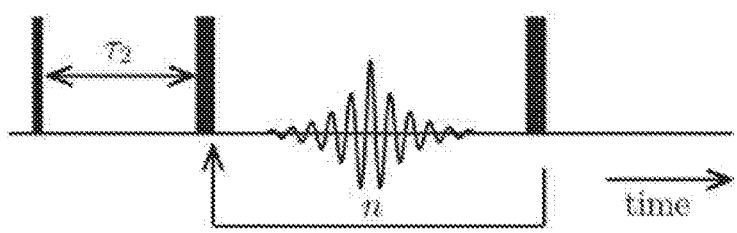

The change in magnetization is monitored using the inversion recovery method illustrated in FIG. 16-1. In particular, FIG. 16-1 is a schematic illustration of the pulse sequence for an inversion recovery measurement of $T_1$. The inversion recovery sequence also includes an optional homospoil gradient pulse (gray trapezoid) that may be included when pulsed field gradients are available.

Transverse magnetization decays over time as the spin ensemble loses phase coherence due to dipolar interactions, heterogeneities in the background magnetic field, and other terms in the nuclear spin Hamiltonian. This process is described by the exponential time constant $T_2$. At low field, where the static magnetic field is inhomogeneous, the CPMG pulse sequence (see FIG. 16-2) is used to generate a train of spin echoes of temporal separation $t_c = 2\tau_2$. The decay of the echo maxima is given by:

$$\frac{M(2n\tau_2)}{M(0)} = \exp\left\{-\frac{nt_e}{T_2}\right\}$$

In the above equation, n represents the number of spin echoes.

The observed NMR signal amplitude following a single excitation pulse (nominally 90°) decays over time as the spin ensemble loses phase coherence in the x-y plane due to local magnetic field fluctuations. These fluctuations arise from dipolar interactions, heterogeneities in the background magnetic field, and other terms in the nuclear spin Hamiltonian. The observed FID is governed by the exponential time constant $T_2^*$ as:

$$\frac{1}{T_2^*} = \frac{1}{T_2} + \gamma \Delta \chi B_0 + \gamma \Delta B_0$$

In the above equation, $\gamma$ represents the gyromagnetic ratio, $\Delta B_0$ is the instrument-specific field inhomogeneity, and $\Delta \chi$ is the solid/liquid magnetic susceptibility contrast. The true transverse relaxation time $T_2$ is typically longer by orders of magnitude than $T_2^*$ and so can be ignored in some embodiments.

The magnetic susceptibility varies in space and a strict exponential magnetization decay according to:

$$\frac{M(t)}{M(0)} = \exp\left\{-\frac{t}{T_2^*}\right\}$$

This is observed when the distribution of local field fluctuations is Gaussian. Empirically, this assumption can hold for drilling fluids, where the magnetic susceptibility contrast arises primarily from the presence of barite and iron contaminants suspended in the fluid. The equation above leads to an empirical measure of magnetic susceptibility by NMR as:

$$\Delta \chi_{app} = \frac{1}{T_2^*} \frac{1}{\gamma B_0}$$

The measurement of $T_2^*$, assuming the FID decays with a single exponential relaxation time, therefore, leads to an indication of the average magnetic susceptibility contrast and hence the iron contamination in the sample. A minimum acceptable $T_2^*$ can be defined for practical measurements, as described herein. If the magnetic susceptibility contrast is too severe, the local magnetic field gradients can result in a diffusive contribution to the $T_2$ measurement (even in a $T_1$-$T_2$ correlation) that limits or potentially prevents the determination of quantitative liquid volumes. However, a measurement of $T_2^*$ during the NMR measurements can allow the system and/or operator to determine the reliability of the measurements and potential for correction if the $T_2^*$ measurement is deemed too high to be considered a "good" sample.

Data processing is achieved by solving the Fredholm integral equation describing the decay of the NMR signal to generate a smooth distribution of relaxation times. Various computational methods can be used to extract a smooth solution from data described by a sum of exponential rate constants in the presence of noise, and many of these methods employ regularization in some form. Some of these methods can be extended to two dimensions. Illustrative examples of smooth 2D distributions obtained on drilling fluids are shown in and described in relation to FIG. 5-1 through 5-5.

Other data manipulation stages may be included prior to numerical inversion, as desired. For example, multiple points acquired in each spin echo may be averaged to stack the data in a 2D array for the inversion code to process. Also, CPMG or FID data may be compressed (e.g., using window sums) to reduce the computational requirement on the processor during the numerical inversion or NNLS fittings processes.

Interpretation of the acquired NMR data can be based on integrating the regions of the smooth 2D associated with oil and water. The total signal amplitude may be obtained by integrating over the entire 2D distribution, and this amplitude can be considered equivalent to acquiring the NMR signal at zero time (i.e., no relaxation), which is virtually impossible in practice. By fitting the data, the decaying signal can be projected back to the time origin, as illustrated in FIG. 17 (composed of FIGS. 17-1 and 17-2).

OWR in the present disclosure can therefore be estimated in drilling fluids by correlating the oil content to the average relaxation time ($T_1$ or $T_2$), integrating over regions of 1D relaxation time distribution ($T_1$, $T_2$, or $T_1/T_2$), or by comparing the NMR signature of a drilling fluid of unknown composition to a reference fluid of known composition. Such processes can also include using a machine-learning approach to identifying the oil and water signals.

Figures 1, 17:
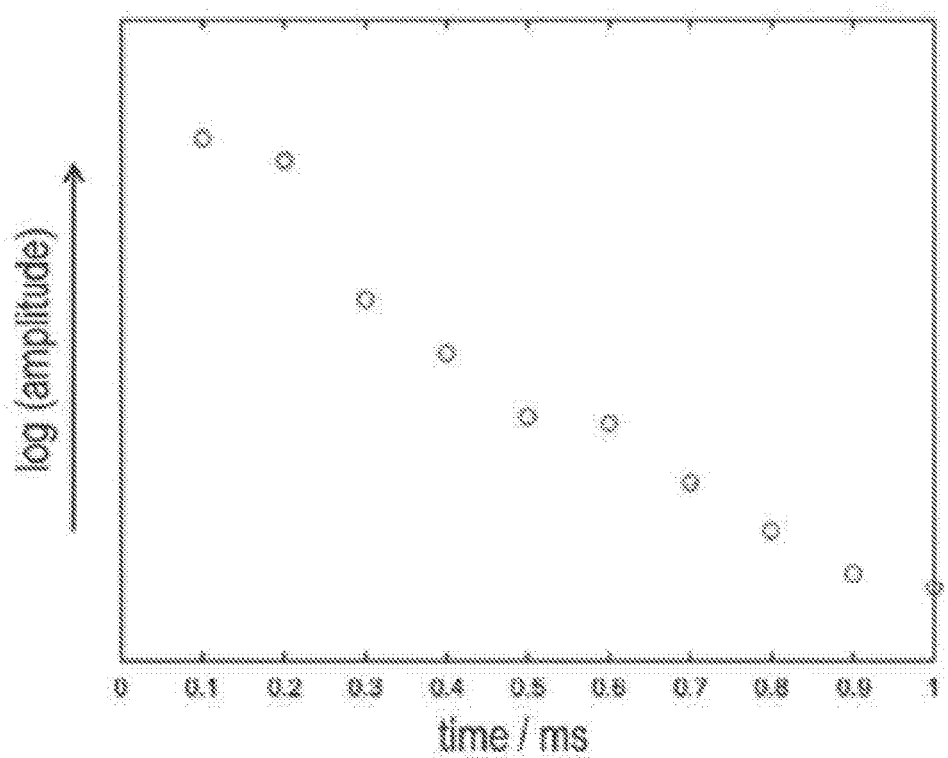
Figures 2, 17:
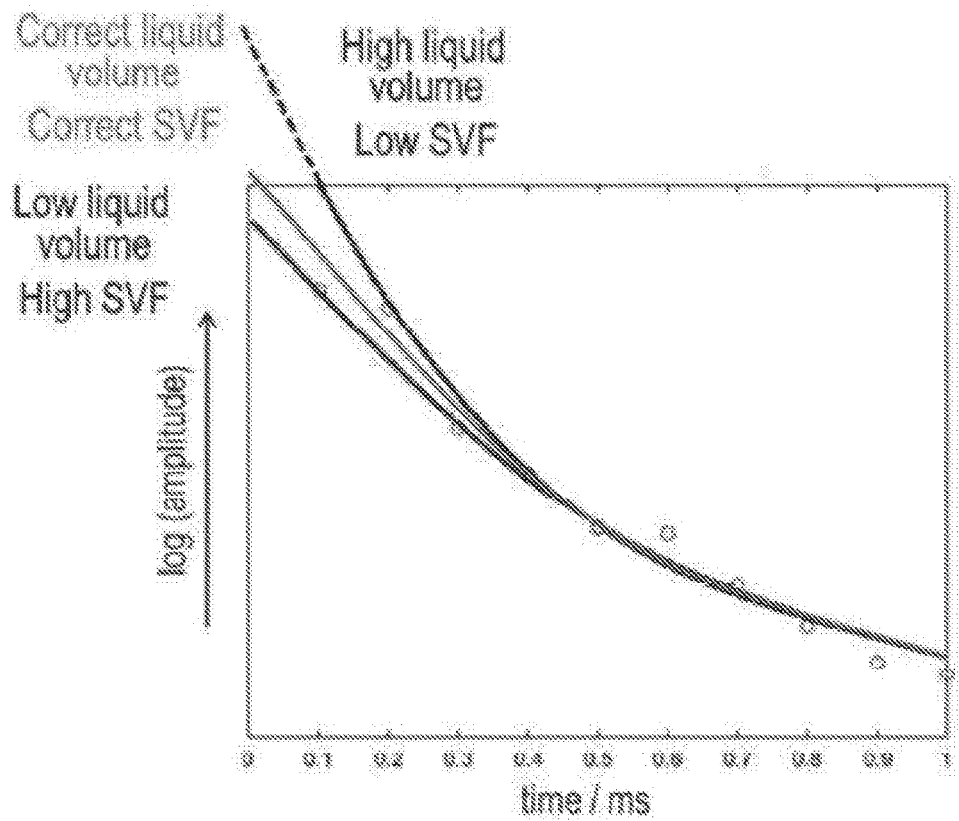

FIG. 17 illustrates examples of fitting errors that can arise due to oscillation of CPMG echo amplitudes. FIG. 17-1 illustrates the raw echo amplitudes as recorded from a CPMG measurement. FIG. 17-2 illustrates the projected zero-time amplitudes depending on the number of echoes used in the fit.

A feature of CPMG echo trains acquired in inhomogeneous fields can include a zig-zag pattern on the early echoes, as seen in FIG. 17-1. This effect arises predominantly from imperfect RF pulses and phase distortions in the spin ensemble. Due to this feature, the implementation of the CPMG sequence can include discarding some echoes (e.g., odd numbered echoes). Discarding this information will also, however, discard some potentially valuable information, especially when the measured $T_2$ is short. To overcome a challenge of underestimated liquid volumes, resulting in a potentially significant overestimate of the solids fraction (often +10%), the 2D experiment can be repeated three times using: (a) all CPMG echoes; (b) echoes 2 to N; and (c) using echoes 3 to N. The typical fits in each case are illustrated in FIG. 17-2 with the colored lines corresponding to conditions (a) red, (b) green, and (c) purple. In some implementations, the inverted data set that gives the largest total integral out of the three is taken to be correct.

Figures 1, 18:
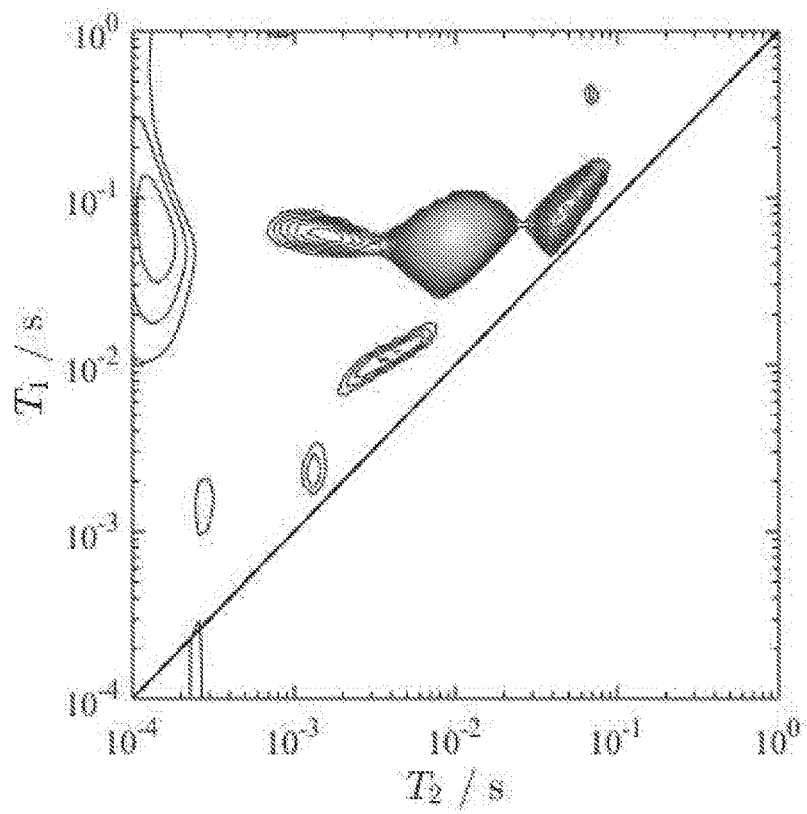
Figures 2, 18:
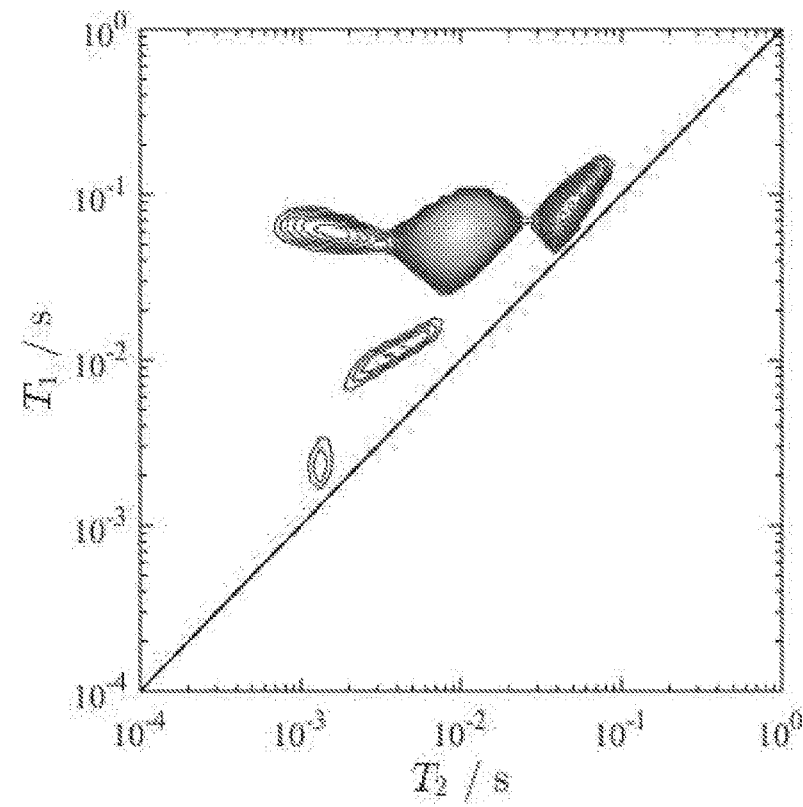

Next, any low-amplitude features and unphysical artifacts present in the $T_1$-$T_2$ correlation can be eliminated. For instance, FIG. 18 (composed of FIGS. 18-1 and 18-2) illustrates the $T_1$-$T_2$ correlation of an oil-based drilling fluid before (FIG. 18-1) and after (FIG. 18-2) removal of low-level features and unphysical artifacts. This removal can be achieved in an automated interpretation by removing components outside the reasonable observable bounds of the experiment (e.g., relaxation times less than $t_e/2$), unphysical artifacts with $T_2 > T_1$ (given the positivity constraint on the distribution), and components below an arbitrary critical significance threshold, typically a factor $10^{-6}$ below the normalized maximum amplitude. These components contribute to the overall signal amplitude, but typically correspond to the numerical inversion scheme attempting to fit an exponential kernel function to non-exponential data. As such, based on empirical observation, they generally are not uniquely associated with the fluid phases present and in order to calculate the OWR, and are removed in some embodiments.

The many possible drilling fluid formulations (see for example FIG. 5-1 through FIG. 5-5) may complicate assigning each signal component to part of the drilling fluid formulation, as such may include extensive modification of the sample. An assignment may not be rigorously universal between similar formulations. Instead, a robust interpretation can be achieved by assigning the largest peak in the distribution to the continuous phase (oil in OBM, SBM or water in DEM, WBM) and the other components to the discontinuous (i.e., emulsified) phase (water in OBM, SBM or oil in DEM). A special case is WBM, where the entire signal is associated with water and there is no discontinuous phase. To achieve this assignment in an automated interpretation, the maximum peak amplitude can be identified in the $T_1$-$T_2$ plot. A search can then made along the x- and y-axes around this point to identify where the peak drops to 50% of its maximum amplitude. A rectangular area is defined based on these ranges. This box may then expanded by a fixed value (e.g., doubled on each axis) and the integral of the signal within the box may be taken to be the continuous liquid fraction. Other signals in the plot (outside the box) are associated with the discontinuous (emulsified) liquid fraction, where appropriate. In some implementations improved peak selection can be obtained by fitting a 2D Gaussian or Voigt function to the distribution, centered on the peak maximum, to reduce contributions from overlapping peaks. In still further implementations an image processing approach can be taken whereby the contour describing the surface of the peak at 50% amplitude can be expanded uniformly in the XY plane to capture an accurate peak shape. Through empirical review these approaches provide reasonable and consistent estimates of the OWR across a wide range of fluid types.

The oil, water, and solids volume fractions can be calculated based on a pre-determined HI for each liquid phase and the pre-determined total measurable sample volume (defined by the diameter of the flow line and the length of the sensitive region of the RF probe).

The NMR signal amplitude is proportional to mass not volume. In some embodiments, at approximately 20° C. the same volume of low-viscosity oil and water provides approximately the same signal amplitude. However, in operation, the drilling fluid entering the device may be at elevated or reduced temperature, so the volumetric HI calibration value may have a liquid density correction applied. The sample temperature could be controlled (as well as the magnet temperature) in some embodiments. In some embodiments, the flow line temperature is monitored, and a density correction is applied to the HI indices. In some embodiments, the small volume (e.g., <1 ml) and mass of the sample measured in the experimental system may equilibrate to the temperature of the thermally regulated magnet. A short delay (1 to 2 minutes) could be enforced between filling the flow lines and running the experiment to allow the sample temperature to equilibrate with the set-point of the magnet. An independent measure of sample temperature is optionally used in some embodiments.

Figure 19:
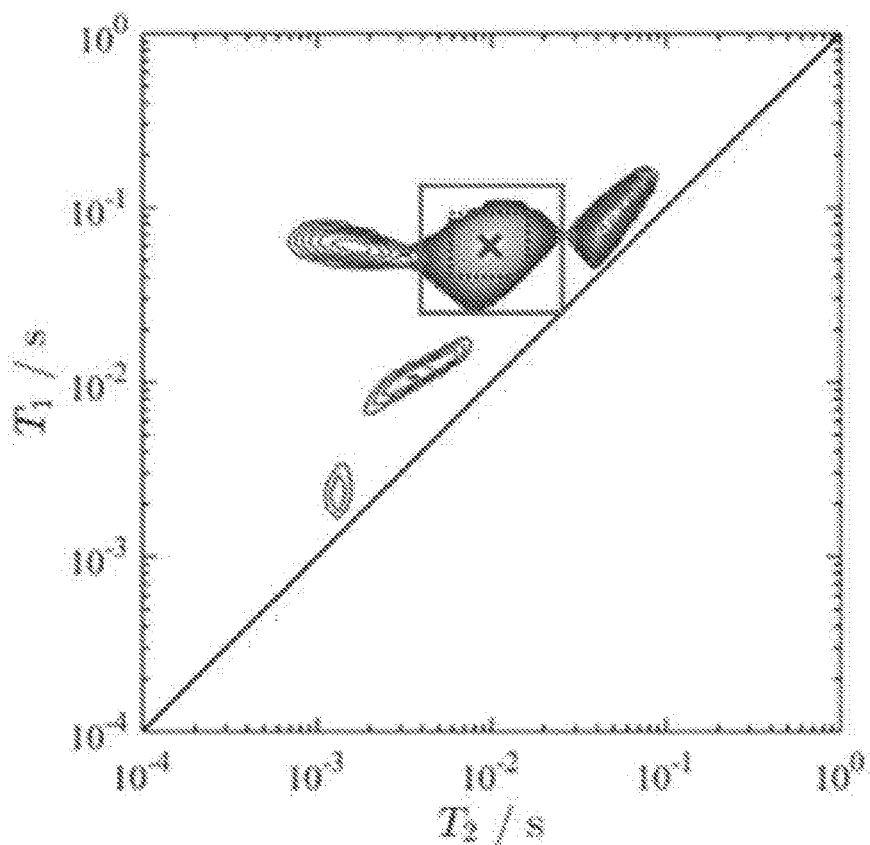
FIG. 19 is a plot illustrating the assignment of the continuous liquid phase signal and designating the maximum peak position, 50% peak intensity, and peak locations, according to embodiments of the present disclosure.

FIG. 19 illustrates the automatic assignment of the continuous liquid phase signal, with the maximum peak position determined (red cross). The 50% peak intensity is located (dotted red box) and then expanded to encompass the peak (solid red box). The integral of signal inside this box is taken to be proportional to the continuous liquid phase.

A variety of other complementary measurements may also be made. For instance, in order to provide the ratio of LGS to HGS, other measurements may be included. Such measurements may include the drilling fluid density, the lime concentration in the drilling fluid, and the calcium chloride and sodium chloride salt concentrations in the brine. Once these parameters are known, the LGS to HGS is readily calculable.

In a combined NMR digital retort tool that is included in a mud rheology device, the drilling fluid density can be quickly or even immediately available from an incorporated Coriolis meter. In a standalone NMR digital retort tool, the drilling fluid density can be input by an operator or provided via a separate rheology device.

NMR can conceivably also be used to detect some of the other parameters of interest, including those used in determining an LGS/HGS ratio. For instance, there are several resonant "X" nuclei of interest that could theoretically be measured in addition to $^1$H, including $^{23}$Na, $^{35}$Cl, and $^{43}$Ca. Other nuclei not typically found in drilling fluids can also be detected. Of these mentioned, $^{35}$Cl may be of particular interest as it provides the ability to directly replace the chemical titration method currently used. This nucleus has a spin-3/2, 76% natural abundance, and a gyromagnetic ratio $\gamma_{35}=2.62\times10^7$ rad T$^{-1}$s$^{-1}$ ($\gamma_{35}/\gamma_1=0.098$).

$^{35}$Cl may be detected at a resonance frequency of approximately $f_0=400$ kHz. Prior research has discussed the existence of $^{35}$Cl detection at low field, although there may be some challenges associated with detecting nuclei with low gyromagnetic ratio. This can, however, largely be addressed in the RF probe design by providing increased power and lower recovery times. Conversely, the sensitivity of $T_2$ relaxation time to diffusion through local magnetic field gradients decreases with the ratio $\gamma_{35}/\gamma_1$ squared, so a higher (and potentially significantly higher) static magnetic field strength could be employed for the $^{35}$Cl measurement (compared to $^1$H) without detrimental effect. Signal-to-noise ratio is also a consideration, and specifically the detectable signal, given the reduced natural abundance of $^{35}$Cl (compared to $^1$H at 100%), the total volume of brine in the drilling fluid (especially when emulsified in OBM or SBM formulations), and the relatively few chlorine nuclei in the brine (compared with hydrogen nuclei). Considering these factors, a separate NMR instrument could be developed for a dedicated $^{35}$Cl measurement. Alternatively, dual use magnet designs may be considered to overcome some of these limitations of a single instrument. $^{37}$Cl is also a spin-3/2 resonant nucleus, but has a much lower natural abundance, and lower gyromagnetic ratio, than $^{35}$Cl so it may be detected, but may not be preferred for some embodiments.

The detection of $^{43}$Ca could also be useful, given that many drilling fluids are formulated with calcium salts. A solid-state calcium measurement could also be used to determine the lime content, Ca(OH)$_2$; however, as this resonant isotope of calcium has a natural abundance of <0.2%, quantitative volumetric assay based on an NMR experiment may not be practical for all field instruments.

The resonant isotope of sodium, on the other hand, has 100% natural abundance and a gyromagnetic ratio $\gamma_{23}=7.08\times10^7$ rad T$^{-1}$ s$^{-1}$ ($\gamma_{23}/\gamma_1=0.27$). $^{23}$Na could be detected at a frequency of $f_0=1.1$ MHz in some embodiments. Further, sodium detection has been demonstrated previously at low field, and could be practical to deploy for bulk liquid samples such as drilling fluids. Like $^{35}$Cl detection, the sodium measurement could also benefit from being deployed at higher field.

Sodium salts can accumulate from formation water during drilling. Therefore, a combined measure of quantitative chloride and sodium ion content could improve the estimate of salt content in the brine. Any chloride not associated with sodium would generally be associated with calcium, and so the calcium content could be inferred that way. The relaxation time and diffusion coefficient of the water (and dissolved ions) are also sensitive to the total dissolved solids content, but these parameters may be influenced by other components of the drilling fluid and developing robust correlation across all drilling fluids may be impractical, but may be performed for limited drilling fluids. If multiple X-nuclei are to be measured with the same NMR instrument, a dual or triple resonance probe could be employed. Such an instrument could include the ADFP upgrade, and dual resonance $^{23}$Na/$^1$H probes have been constructed previously.

As discussed herein, an estimate of the solid/liquid magnetic susceptibility contrast in a drilling fluid may be obtained from an NMR FID experiment. This measurement can provide information on the iron content of the sample. Iron could possibly gradually accumulate at the fringes of the static magnetic field (where $\nabla B_0$ is large) during the fill and flush stages. Based on the NMR measurement alone, it may be difficult to determine if the iron content was changing due to the sample or due to accumulation of material. Thus, a separate magnetic susceptibility measurement, applied to the flow line prior to the magnet, can be used in some embodiments to provide differentiation as this will be sensitive to primarily or potentially only the iron in the sample. For flow line measurements, a susceptibility bridge can be employed where the modulation in frequency of an alternating current (AC) induction field is measured. Additional complementary measurements include the sample temperature and the drilling fluid (e.g., as a function of temperature).

To further the discussion herein, excessive ferrous/iron content in the drilling fluid may create challenges in measuring oil/water/solids ratios. The FID measurement described herein can be used to estimate the iron content and raise a flag/error if the sample is outside a predefined tolerance level. In extreme cases, the interference could almost entirely inhibit the detection of a $^1$H signal. The signal deriving from the $^{19}$F resonant nuclei in the RF probe former (e.g., formed of PTFE) could be used to distinguish between an absence of $^1$H signal or a failure of the RF system.

In some embodiments, automated correction and/or machine learning (ML) can be used to refine data determined to be above a threshold value of the FID measurement or other magnetic susceptibility measurement. For example, a ML model can be used to determine a correction that may be applied to the measured data to deconvolute multiple peaks within the broadened continuous phase peak. The ML model includes an input layer that receives at least one training dataset. In some embodiments, at least one ML model uses supervised training. Supervised training allows the input of a training dataset with at least one known component and sample properties and allows the machine learning system to develop correlations between the known components and known sample properties to identify the peaks in the training dataset. In some embodiments, at least one ML model uses unsupervised training. Unsupervised training can be used to draw inferences and find patterns or associations from the training dataset(s) without known components. For example, instances from samples with high magnetic susceptibility may have characteristic shoulders to the individual spectra around the peak(s). In some embodiments, unsupervised learning can identify clusters of similar peak shapes and/or sample properties for a variety of training datasets and allow the ML system to extrapolate the peak shapes and constituent components from other datasets. In some embodiments, semi-supervised learning can combine benefits from supervised learning and unsupervised learning.

In some embodiments, gas bubbles in a sample may appear as "not liquid", and hence could be interpreted as solids for the solids volume fraction calculation. As the drilling fluid may be at atmospheric pressure before entering the flow line (and during measurement), no significant outgassing could be expected to occur. If the flow line is mounted in a vertical or generally vertical orientation in the magnet, and the dense drilling fluid is injected from the base, then air may be displaced from the measurement of the flow line. In contrast, a horizontal arrangement may tend to trap bubbles in the measurement section. Of course, other methods for pushing bubbles out of a measurement section may also be used.

Figure 20:
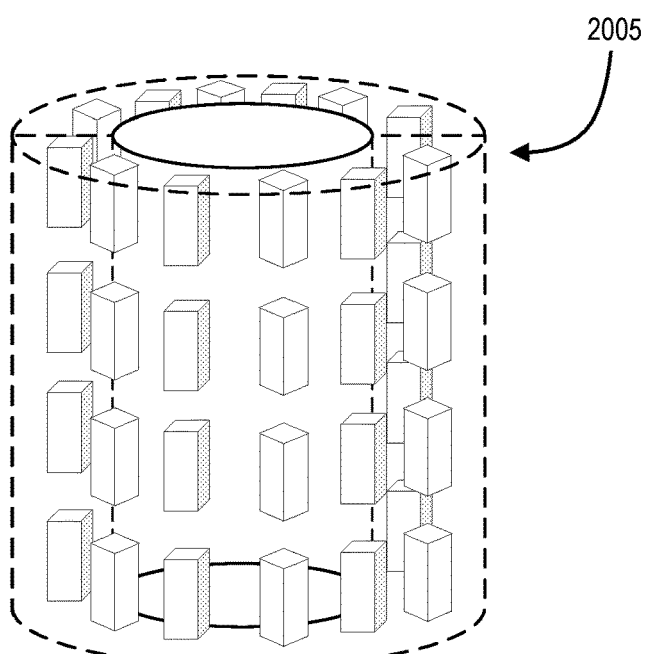
FIG. 20 is a perspective view of a cylindrical Halbach magnet array, according to embodiments of the present disclosure.

Hardware components and methods described herein are intended to be illustrative, and a person of ordinary skill in the art will appreciate that other components or method steps and acts can be used to perform similar or the same functions. For instance, while a magnet of a retort measurement tool is described as having a pole-piece design, other suitable magnet concepts exist, including cylindrical Halbach arrays 2005 of FIG. 20. Such a magnet may generally be larger than a pole-piece magnet, and potentially more difficult and expensive to construct, but may provide other desirable features. In still other embodiments, a cryogen-free superconducting magnet may be used.

The strength of the magnetic field could also be adjustable in some embodiments. A weaker magnetic field (e.g., $B_0$=50 mT, $f_0$=2 MHz for $^1$H) could slightly reduce the detrimental influence of ferrous contamination (compared to a system at $B_0$=100 mT). Increasing the magnetic field (e.g., $B_0$=500 mT, $f_0$=20 MHz for $^1$H) could provide significant improvements in signal-to-noise ratio, although detrimental effects of ferrous contamination could also be significant and in some cases limit or even prevent quantitative determination of liquid volumes.

Much stronger magnetic fields (e.g., $B_0$=2 T, $f_0$=80 MHz for $^1$H) may also be available for chemical spectroscopy. Such magnets could be used in an NMR retort tool of the present disclosure to identify liquid components (oil, water, surfactants, etc.) in the drilling fluid (or salts with X-nucleus detection as noted above). In some embodiments, these stronger magnetic fields operate in the absence of some or potentially all solids (barite, clay, drill solids).

Like the magnet, various different RF probes may be used in different embodiments. The RF probe can be tuned using an LCR circuit (a "tank" circuit). In a test instrument, the ADFP concept was used rather than a tank circuit, which provided improved signal-to-noise ratio (at least a factor ×2) for the same sample volume, reduced probe recovery time ("dead" time) after an RF pulse, reduced RF power requirement for the same pulse duration, and immunity to capacitive loading from conductive samples (i.e., detuning in the presence of, e.g., a high-salinity brine). Other probe options are available, including fast switching probes.

The magnet temperature control described herein was used in an example NMR retort tool and provided a robust method of maintaining stable and reliable measurements. This control provided the option to heat but not cool, and to therefore maintain a stable temperature the set-point was above the ambient temperature, while in other embodiments, the magnet temperature control may include cooling in addition to or in the alternative to heating. In some embodiments, it may be desirable to have multiple pre-selected set-points (and corresponding RF probe tuning parameters) that can be chosen manually or automatically based on the external temperature. Nominal set-points might include 20° C., 35° C., and 50° C., for example. In this way, the magnet temperature control power can be efficiently used to achieve the desired set-point.

In some embodiments, rather than controlling the magnet temperature, other methods may also be used. For example, it is possible to leave the magnet temperature unregulated and use whatever magnetic field strength is available at the time. This technique could be combined with a more robust or adaptable RF probe as the resonance frequency of the NMR instrument could then drift outside the bandwidth of the tuned probe. In combination with this feature, it may be advisable to also use one or more of an automatic probe tuning facility or a non-resonant probe. Other methods for controlling the magnetic field also exist, such as the use of a tunable $B_0$ system.

As discussed, the flow line of an example system may be arranged to pass vertically through an NMR magnet. This configuration can be used, for instance, to reduce the likelihood of gas bubbles being present in the measured volume. In some embodiments, the magnet could be rotated so the flow line passes horizontally through the probe bore, or at any angle in between.

In some embodiments, the NMR system functions in a "batch" mode, where the sample is loaded, the flow is stopped for the duration of the measurement, and then the sample is removed. In some embodiments, the sample flows continuously through the probe to provide a time-averaged measurement. By maintaining a sufficiently low flow rate, such as a flow rate that ensures a relatively homogeneous sample composition, a reasonable data quality is achieved. In other embodiments, a sample is placed in a tube (optionally made from borosilicate glass) and placed in the probe bore by the operator (or automated loading mechanism).

A set of NMR pulse sequences have been described and used experimentally. However, many pulse sequences and modifications thereof could be used to perform the same or a similar function. For example, a $T_2$ relaxation time could be determined from a solid echo train (also known as a quadrature echo train). Similarly, $T_1$ could be measured by "saturation recovery" or a "double-shot" sequence.

In embodiments contemplated herein, smooth distributions of relaxation times in one and two dimensions were generated. Alternatively, instead of producing a smooth distribution, discrete relaxation time components may be determined from the data.

In some embodiments, the workflow or operation of a digital retort tool can include the following steps. An example initial step can include a calibration step. As part of the calibration (which can be run on deployment and at regular/occasional intervals as part of routine maintenance), the instrument can be switched on and the magnet temperature can be allowed to stabilize. In some embodiments, the flow line/chamber can be filled with a calibration fluid such as doped water, base oil, cleaning fluid, other fluids, or combinations thereof. Thereafter, a calibration cycle can be initiated using a user interface. While the tool is operating, magnet temperature can be automatically or manually checked to ensure the temperature is within a desired range. If not, the temperature can be flagged/reported, and the system can wait until the temperature stabilizes.

While the operation is running, a reference signal can be obtained through the search coil, and the RF amplifier and probe can be checked to ensure proper operation. The FID can then be acquired. This may include checking the signal amplitude and signal-to-noise ratio to ensure a sample is present and setting of the resonance frequency. If the change in resonance frequency is outside of a pre-set tolerance/threshold, the FID acquisition can be repeated and the resonance frequency can again be set.

Within the calibration, the RF pulse durations can also be calibrated using an appropriate pulse sequence. Desirable or optimum durations for 90° and 180° tip angle pulses can be determined according to known or proprietary methods. Such a process can take up to 30 minutes in some embodiments. Additionally, a CPMG echo train can be acquired, and the signal decay can be converted to a $T_2$ distribution using a numerical inversion technique. The distribution is integrated to provide a total signal amplitude, which is in turn converted to a liquid volume using an appropriate HI value and calibration constant (e.g., signal per unit volume liquid). The flow line can be evaluated to ensure the flow line is full, and that the total liquid volume is within the expected tolerance. Stored parameters may then be stored in internal memory for subsequent measurements.

Following calibration, the digital retort instrument may be used for standard operations—whether as a stand-alone tool or integrated into another tool (e.g., a mud rheology tool). For such operations, the flow line/chamber can be filled with sampled fluid. Optionally, the drilling fluid type (e.g., OBM, SBM, DEM, WBM) is set via a user interface or is automatically detected. The measurement cycle may also be initiated manually via a user interface or automatically. Through the measurement stage, the magnet temperature may be monitored occasionally/regularly to ensure temperature is within the desired range. A reference signal can also be obtained through the search coil, and the RF amplifier and probe can be checked to ensure they are functioning.

The FID can be acquired, and the signal amplitude and signal-to-noise ratio checked, to ensure the sample is present. As during the calibration, the resonance frequency can be set and if a change is outside a pre-set tolerance, the FID acquisition and setting of the resonance frequency can be repeated. The acquired FID can then be fitted to determine $T_2^*$ using an appropriate algorithm (e.g., nonlinear least squares (NNLS) algorithm). If $T_2^*$ is below a pre-set value (e.g., $10^{-4}$ s) (i.e., magnetic susceptibility contrast in sample is above a pre-set value which can be indicative of high iron contamination), a data quality flag can be raised. In some embodiments, if $T_2^*$ is below a pre-set value, the system may apply or offer to apply a correction or deconvolution to the measured spectra, as described herein.

In some embodiments, a CPMG echo train is acquired. The signal decay is converted to a $T_2$ distribution using an appropriate numerical inversion technique. Experimental parameters for $T_1$-$T_2$ measurement are estimated based on resulting $T_2$ distribution (list of $T_1$ recovery delays, recycle delay between scans=5×$T_1$, number of repeat scans to achieve useful SNR, number of echoes for the CPMG train, etc.) and processing parameters (range of $T_1$ and $T_2$ to fit).

A $T_1$-$T_2$ data set can be acquired using inversion recovery-CPMG pulse sequence, and data quality issues can be checked (e.g., signal amplitude does not increase monotonically with increase $T_1$ recovery time). If the data has sufficiently good quality, it is converted to a $T_1$-$T_2$ relaxation time distribution using an appropriate numerical inversion technique. If the data quality is low, the data acquisition can be repeated. An interpretation method can be applied to the $T_1$-$T_2$ relaxation time distribution, which is integrated over relevant ranges of the 2D distribution to obtain signal amplitudes for oil and water (as appropriate for sample selection) and total signal for solids determination. In some embodiments, signal amplitudes can be converted to volumes using pre-set HI values and calibration constants (e.g., signal per unit volume liquid).

The OWS can then be reported. In some embodiments, when additional information is available (e.g., drilling fluid density, salt content of brine), solids volume can be converted to HGS and LGS volume fractions, and the HGS to LGS ratio can be reported (e.g., by recording results displayed on the user interface).

NMR digital retort tools and NMR methods of the present disclosure can be used in a variety of applications and can include various features. For instance, an NMR digital retort tool and method may be able to provide an OWS measurement within minutes (e.g., 10-30 minutes) rather than in hours (e.g., 3 hours). Further, the drilling fluid can be evaluated without modification or preparation of the samples (e.g., without boiling). Drilling fluid can also be confined to a flow line and can be separate from electronics, allowing the measurement tool to be ATEX compliant.

The tools and methods of the present disclosure can also be used for all types of drilling fluids and other liquids (e.g., to determine water cut in production fluids), and calibration may be fully automated to allow self-checking and self-calibrating with potentially zero user input. Operator error can also be taken out as the results can be operator-independent and can be obtained by someone other than an experienced mud engineer.

Another aspect of the present disclosure is that it can be modified at any time to include novel interpretational aspects or expanded (with or without hardware upgrades) to obtain new interpretations, advanced NMR measurements (e.g., droplet sizing, chlorine content, etc.), and other complementary measurements. Iron contamination is also not a show-stopper for this system, particularly at levels so far encountered in real drilling fluid samples. Excessive contamination can be detected by the NMR instrument (e.g., with a magnetic susceptibility test), allowing an automatic stop to occur to the process, or to raise a flag on the data quality when iron contamination becomes unacceptable. Additionally, OWR measurements and interpretation based on 2D $T_1$-$T_2$ correlation data sets can be used and more reliable than interpretations based on 1D data sets.

In some embodiments, the methods of the present disclosure may be executed by a computing system. For instance, a computing system may include a computer or computer system that is an individual computer system or an arrangement of distributed computer systems. The computer system can include one or more analysis modules that are configured to perform various tasks according to some embodiments, such as one or more methods disclosed herein. Example modules or computing systems may be in the form of special-purpose tools (e.g., sensor packages, RF probes, RF amplifiers, inversion tools, etc.). To perform these various tasks, the analysis module executes independently, or in coordination with, one or more processors, which are connected to one or more computer-readable media. The processors are optionally connected to a network interface to allow the computer system to communicate over a data network with one or more additional computer systems and/or cloud computing systems that may or may not share the same architecture, and may be located in different physical locations. For instance, one computer system may be located on a drilling rig adjacent the wellbore, another may be in a doghouse or other location at a wellsite, another may be in a remote computing center, another may be in a cloud-computing facility or data center, and any may be located in varying countries on different continents.

A processor may include a microprocessor, microcontroller, processor module or subsystem, programmable integrated circuit, programmable gate array, or another control or computing device. Additionally, while computer-readable media may be within a computer system, in some embodiments, computer-readable media may be distributed within and/or across multiple internal and/or external enclosures of a computing system and/or additional computing systems. The computer-readable media may be implemented as one or more computer-readable or machine-readable storage media, transmission media, or a combination of storage and transmission media.

As used herein, "storage media", "computer-readable storage media," and the like refer to physical media that stores software instructions in the form of computer-readable program code that allows performance of embodiments of the present disclosure. "Transmission media", "computer-readable transmission media," and the like refer to non-physical media which carry software instructions in the form of computer-readable program code that allows performance of embodiments of the present disclosure. Thus, by way of example, and not limitation, embodiments of the present disclosure can include at least two distinctly different kinds of computer-readable media, namely storage media and/or transmission media. Combinations of storage media and transmission media should be included within the scope of computer-readable media.

To further illustrate the distinct nature of storage media and transmission media, storage media may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLURAY® disks, or other types of optical storage, or solid state drives, or other types of storage devices.

Transmission media may conversely include communications networks or other data links that enable the transport of electronic data between computer systems and/or modules, engines, and/or other electronic devices. When information is transferred or provided over a communication network or another communications connection (either hardwired, wireless, or a combination of hardwired or wireless) to a computing device, the computing device properly views the connection as a transmission medium. Transmission media can therefore include a communication network and/or data links, carrier waves, wireless signals, and the like, which can be used to carry desired program, code means, or instructions.

Note that the instructions discussed above may be provided on one computer-readable or machine-readable medium or may be provided on multiple computer-readable or machine-readable media distributed in a large system having possibly plural nodes. Such computer-readable or machine-readable medium or media is (are) considered to be part of an article (or article of manufacture). An article or article of manufacture may refer to any manufactured single component or multiple components. The computer-readable medium or media may be located either in the machine running the machine-readable instructions or located at a remote site from which machine-readable instructions may be downloaded over a network for execution. Further, where transmission media is used, upon reaching various computing system components, program code in the form of computer-executable instructions or data structures can be transferred automatically or manually from transmission media to storage media (or vice versa). For example, computer-executable instructions or data structures received over a network or data link can be buffered in memory-type storage media (e.g., RAM) within a network interface module (MC), and then eventually transferred to computer system RAM and/or to less volatile storage media (e.g., a hard drive) at a computer system. Thus, it should be understood that storage media can be included in computer system components that also (or even primarily) utilize transmission media.

It should be appreciated that described computing systems are merely examples of computing systems, and that a computing system may have more or fewer components than described, may combine additional components not described, or may have a different configuration or arrangement of the components. The various components of a computing system may be implemented in hardware, software, or a combination of both hardware and software, including one or more signal processing and/or application specific integrated circuits.

Further, the steps in the processing methods described herein may be implemented by running one or more functional modules in information processing apparatus such as general-purpose processors or application specific chips, such as ASICs, FPGAs, PLDs, or other appropriate devices. These modules, combinations of these modules, and/or their combination with general hardware are included within the scope of the present disclosure.

Computational interpretations, models, and/or other interpretation aids may be refined in an iterative fashion; this concept is applicable to the methods discussed herein. This may include use of feedback loops executed on an algorithmic basis, such as at a computing device, and/or through manual control by a user who may make determinations regarding whether a given event, action, template, model, or set of charts has become sufficiently accurate for the evaluation of the frequency data under consideration.

The terms "couple," "coupled," "connect," "connection," "connected," "in connection with," and "connecting" refer to "in direct connection with" or "in connection with via one or more intermediate elements or members." In the claims, means-plus-function clauses are intended to cover the structures described herein as performing the recited function and not merely structural equivalents, but also equivalent structures. It is the express intention of the applicant not to invoke functional claiming for any limitations of any of the claims herein, except for those in which the claim expressly uses the words "means for" or "step for" together with an associated function.

Although a few example embodiments have been described in detail above, those skilled in the art will readily appreciate that many modifications are possible in the example embodiments without materially departing from the scope of the present disclosure. Accordingly, any such modifications are intended to be included within the scope of this disclosure.

What is claimed is:

1. A method for determining volume fractions in a drilling fluid, the method comprising:
   flowing a drilling fluid sample through a flow line of a digital retort tool disposed at a surface, wherein the drilling fluid sample is from a drilling fluid at the surface that is entering a wellbore;

upon the digital retort tool receiving a trigger signal, applying a magnetic field to the drilling fluid sample while the drilling fluid sample is flowing through the flow line of the digital retort tool disposed at the surface;

acquiring, with the digital retort tool, nuclear magnetic resonance (NMR) data from the drilling fluid sample while the drilling fluid sample flows through the flow line;

determining volume fractions of at least one liquid phase and at least one solid phase present in the drilling fluid sample from the NMR data with the digital retort tool; and reporting the volume fractions to a user.

2. The method of claim 1, further comprising:
identifying a continuous liquid phase of the drilling fluid sample from the NMR data, and
reporting the continuous liquid phase to the user with a user interface of the digital retort tool.

3. The method of claim 1, wherein determining volume fractions further comprises:
performing a two-dimensional (2D) inversion of the NMR data to create 2D inverted data, and
integrating the 2D inverted data.

4. The method of claim 3, wherein integrating the 2D inverted data fitting a Gaussian or Voigt function in two dimensions to at least one peak in the 2D inverted data and taking an integral of the at least one peak.

5. The method of claim 4, wherein an integral area for integration around the at least one peak is determined by:
finding a position of a maximum peak amplitude in the 2D inverted data;
searching either side of the position on x and y axes to determine when a peak amplitude drops below 50% of the maximum peak amplitude;
defining the integral area based on x and y coordinates of a predetermined percentage of peak amplitude; and
expanding the integral area in at least four directions.

6. The method of claim 5, wherein expanding the integral area includes expanding the integral area based on a contour of a peak surface at the predetermined percentage of peak amplitude uniformly in an x-y plane.

7. The method of claim 1, wherein determining volume fractions further comprises:
using an integral of a T1-T2 correlation map to provide a total liquid volume;
identifying a largest peak in the T1-T2 correlation map and associating the largest peak with a continuous liquid phase;
associating an integral of a region of the T1-T2 correlation map corresponding to the largest peak to provide a first signal proportional to a continuous liquid phase volume;
associating remaining peaks in the T1-T2 correlation map with a discontinuous liquid phase; and
associating an integral of a region of the T1-T2 correlation map corresponding to the remaining peaks to provide a second signal proportional to a discontinuous liquid phase volume.

8. The method of claim 1, further comprising:
obtaining a free induction decay (FID) measurement, and determining a magnetic susceptibility contrast of the drilling fluid sample.

9. The method of claim 8, further comprising if the magnetic susceptibility contrast is above a pre-set value, reporting a data quality flag to the user.

10. The method of claim 8, where the FID measurement is used to:
set a transmission and detection frequency of a spectrometer;
determine a relaxation time $T2^*$ due to local magnetic field fluctuations;
convert the $T2^*$ relaxation time to a value for a solid/liquid magnetic susceptibility contrast in the sample;
determine an iron content of the drilling fluid based on the magnetic susceptibility contrast; and
automatically raise a data quality flag or stop operation if the iron content exceeds a pre-set value.

11. The method of claim 1, further comprising applying a calibration constant and a hydrogen index to convert NMR signal amplitudes to liquid volumes.

12. The method of claim 1, further comprising:
applying a calibration volume of the drilling fluid sample; and
determining solids volume fraction in the drilling fluid sample based on an absence of an NMR signal.

13. The method of claim 1, further comprising using a machine learning model in identifying a fluid type of the drilling fluid sample as oil-based mud (OBM), synthetic oil-based mud (SBM), direct emulsion mud (DEM), or water based mud (WBM) based on a comparison of the NMR data to data sets acquired previously on known samples.

14. The method of claim 1, wherein acquiring NMR data from the drilling fluid sample includes measuring NMR data from at least one 1H nucleus and at least one additional resonant "X" nucleus, wherein the X nucleus is selected from a group consisting of 35Cl, 37Cl, 23Na, and 43Ca.

15. The method of claim 1, further comprising acquiring second NMR data from a second fluid sample, wherein the second fluid sample originates from a different source than the drilling fluid sample.

16. An apparatus for determining volume fractions in a drilling fluid at a rig site, comprising:
a housing comprising an inlet and an outlet;
a flow line disposed in the housing and extending from the inlet to the outlet;
a nuclear resonance magnet (NMR) magnet disposed in the housing and disposed around the flow line, the NMR magnet configured to apply a magnetic field to a drilling fluid sample while the drilling fluid sample flows through the flow line;
a radio frequency probe disposed in the housing;
a spectrometer disposed in the housing;
a computing device disposed in the housing configured to perform data processing and interpretation of NMR data from the spectrometer, wherein the computing device is configured to raise a flag when iron contamination exceeds a specified threshold; and
a user interface disposed on the housing, wherein the user interface is configured to display the flag to a user.

17. The apparatus of claim 16, further comprising a heater to regulate a temperature of the magnet.

18. The apparatus of claim 16, wherein the radio frequency probe is fitted with an active damping feedback pre-amplifier.

19. An apparatus to determine volume fractions in a drilling fluid at a rig site, comprising:
a housing comprising an inlet and an outlet;

a nuclear magnetic resonance (NMR) magnet, radio frequency probe, and compact spectrometer for detection of 1 H resonant nuclei disposed in the housing;

a heater and heater control to regulate a temperature of the magnet disposed in the housing;

a radio frequency power amplifier disposed in the housing;

a flow line disposed in the housing and extending from the inlet to the outlet;

a computer for data processing and interpretation disposed in the housing, the computer being configured to:
 correlate measurement of nuclear spin relaxation times T1 and T2;
 extract NMR signal amplitudes corresponding to continuous and discontinuous liquid-phases in a fluid sample based on an amplitude of relaxation time components while the fluid sample flows through the flow line;
 apply calibration constants and hydrogen indices to convert NMR signal amplitudes to liquid volumes;
 apply a calibration volume of a sample chamber of the flow line and determine solids volume fraction in the fluid sample based on an absence of an NMR signal; and
 calculate the oil, water, and solids volume fractions from the NMR signal amplitudes; and a user interface disposed on the housing, wherein the user interface is configured to display the calculated volume fractions from the computer.

20. The apparatus of claim 19, wherein calculating the oil, water, and solids volume fractions from the NMR signal amplitudes proceeds automatically, without user intervention, and includes:
 generation of T1-T2 two-dimensional correlation by numerical inversion based on a regularized solution to a Fredholm integral equation;
 using an integral of a T1-T2 correlation map to provide a total liquid volume;
 identifying a largest peak in the T1-T2 correlation map and association with a continuous liquid phase;
 associating an integral of a region of the T1-T2 correlation map corresponding to a largest amplitude peak to provide a first signal proportional to a continuous liquid phase volume;
 associating remaining peaks in the T1-T2 correlation map with a discontinuous liquid phase; and
 associating an integral of a region of the T1-T2 correlation map corresponding to remaining peaks to provide a second signal proportional to a discontinuous liquid phase volume.

* * * * *